(12) United States Patent
Russell et al.

(10) Patent No.: US 7,820,376 B2
(45) Date of Patent: Oct. 26, 2010

(54) PROTEIN C POLYMORPHISMS

(75) Inventors: James A. Russell, Vancouver (CA); Keith R. Walley, North Vancouver (CA)

(73) Assignee: University of British Columbia, Vancouver, British, Columbia ( * ) Notice: Subject to any disclaimer, the term of this patent is extended or adjusted under 35 U.S.C. 154(b) by 1001 days.

(21) Appl. No.: 10/515,493

(22) PCT Filed: May 28, 2003

(86) PCT No.: PCT/CA03/00751

§ 371 (c)(1),
(2), (4) Date: Oct. 26, 2005

(87) PCT Pub. No.: WO03/100090

PCT Pub. Date: Dec. 4, 2003

(65) Prior Publication Data

US 2007/0128594 A1 Jun. 7, 2007

Related U.S. Application Data

(60) Provisional application No. 60/383,128, filed on May 28, 2002.

(51) Int. Cl.
*C12Q 1/68* (2006.01)
*C12P 19/34* (2006.01)

(52) U.S. Cl. .............................. 435/6; 435/91.1; 436/63

(58) Field of Classification Search ........................ None
See application file for complete search history.

(56) References Cited

OTHER PUBLICATIONS

Hegele, Arterioscler. Thromb. Vasc. Biol. 2002, vol. 22, pp. 1058-1061.*
Hattersley et al. (Lancet, 2005, vol. 366, pp. 1315-1323).*
Ionnidis (Plost Med, 2005, 2(8):e124).*
Kroese et al. (Genetics in Medicine, vol. 6 (2004), p. 475-480).*
Blamey, S.L, et al. Protein c antigen levels in major abdominal surgery: relationships to deep vein thrombosis, malignancy and treatment with stanozolol. Thromb Haemost (1985) 54(3):622-625.
Faust, S.N, et al. Dysfunction of endothelial protein c activation in severe meningococcal sepsis. New Eng J Med (2001) 345(6):408-416.
Fijnvandraat, K., et al. Coagulation activation and tissue necrosis in meningococcal septic shock: severely reduced protein c levels predict a high mortality. Thromb Haemost (1995) 73(1):15-20.
Fisher, C.J. and Yan, S.B. Protein c levels as a prognostic indicator of outcome in sepsis and related diseases. Critical Care Medicine (2000) 28(9 Suppl):S49-S56.
Foster, D.C., et al. The nucleotide sequence of the gene for human protein c. Proc Natl Acad Sci USA (1985) 82(14):4673-4677.
Griffin, J.H., et al. Protein c, an antithrombotic protein, is reduced in hospitalized patients with intravascular coagulation. Blood (1982) 60(1):261-264.
Hesselvik, J.F., et al. Protein c, protein s and c4b-binding protein in severe infection and septic shock. Thromb Haemost (1991) 65(2):126-129.
Spek, C.A., et al. Two mutations in the promoter region of human protein c gene both cause type I protein c deficiency by disruption of two HNF-3 binding sites. J Biologic Chemistry (1995) 270(41):24216-21.
Taylor, F.B., et al. Protein c prevents the coagulopathic and lethal effects of *Escherichia coli* infusion in the baboon. J Clin Invest (1987) 79:918-925.
Vervloet, M.G., et al. Derangements of coagulation and fibrinolysis in critically ill patients with sepsis and septic shock. Semin Thromb Hemost (1998) 24(1):33-44.
Yan, S.B. and Dhainaut, J.F. Activated protein c versus protein c in severe sepsis. Critical Care Medicine (2001) 29(7):S69-S74.
David, M., et al. "Identification of mutations in 15 Hungarian families with hereditary protein C deficiency", British Journal of Haematology, (2000), 111:129-135.
Espana, Francisco, et al. "Inherited abnormalities in the protein C activation pathway", Pathophysiology of Haemostatis and Thrombosis, (2002), 32:241-244.
Faioni, Elena, M., et al. "Type II protein C deficiency: identification and molecular modelling of two natural mutants with low anticoagulant and normal amidolytic activity", British Journal of Haematology, (2000), 108:265-271.
Gandrille, S., et al. "First de novo mutations in the protein C gene of two patients with type I deficiency:" a missense mutation and a splice site deletion, Blood, (1994), 84(8):2566-2570.
Gandrille, S., et al. "Identification of mutations in 90 of 121 consecutive symptomatic French patients with a type I protein C deficiency", Blood, (1995) 86(7):2598-2605.
Labrouche, Sylvie, et al. "Protein C and protein S assessment in hospital laboratories: which strategy and what role for DNA sequencing?", Blood Coagulation and Fibrinolysis, (2000), 14:531-538.
Le Cam-Duchez, Veronique, et al. "Influence of three potential genetic risk factors for thrombosis in 43 families carrying the factor V Arg 506 to Gln mutation", British Journal of Haematology, (1999), 106:889-897.
Millar, David S, et al. "Molecular genetic analysis of severe protein C deficiency", Hum Genet (2000), 106:646-653.
Naito, Masao, et al. "Defective sorting to secretory vesicles in transgolgi network is partly responsible for protein C deficiency", Circ. Res. (2003), 92:865-872.

(Continued)

*Primary Examiner*—Sarae Bausch
(74) *Attorney, Agent, or Firm*—Browdy and Neimark, PLLC

(57) ABSTRACT

The invention provides methods and kits for obtaining a prognosis for a patient having or at risk of developing an inflammatory condition. The method generally comprises determining a protein C promoter genotype of a patient for a polymorphism in the protein C promoter region of the patient, comparing the determined genotype with known genotypes for the polymorphism that correspond with the ability of the patient to recover from the inflammatory condition and identifying patients based on their prognosis. The invention also provides for methods of identifying other polymorphisms that correspond with the ability of the patient to recover from the inflammatory condition.

8 Claims, 3 Drawing Sheets

OTHER PUBLICATIONS

Reitsma, Pieter H., "Protein C deficiency: summary of the 1995 database update", Nucleic Acids Research, (1996), 24(1):157-159.

Taylor, F.B., "The endothelial cell protein C receptor aids in host defense against *Escherichia coli* sepsis", Blood, (2000), 95(5): 1680-1686.

G. R. Bernard, et al., "Efficacy and Safety of Recombinant Human Activated Protein C for Severe Sepsis," The New England Journal of Medicine, vol. 344, No. 10, Mar. 8, 2001, pp. 699-709.

C. Arnold Spek, et al., "Genotypic Variation in the Promoter Region of the Protein C Gene is Associated with Plasma Protein C Levels and Thrombotic Risk," Arteriosclerosis, Thrombosis, and Vascular Biology, vol. 15, No. 2, Feb. 1995, pp. 214-218.

Martine Aiach, et al., "Complex Association of Protein C Gene Promoter Polymorphism with Circulating Protein C Levels and Thrombotic Risk," Arteriosclerosis, Thrombosis, and Vascular Biology, vol. 19, No. 6, Jun. 1999, pp. 1573-1576.

D. Scopes, et al., "Polymorphic Variation in the Human Protein C (PROC) Gene Promoter Can Influence Transcriptional Efficiency in Vitro," Blood Coagulation and Fibrinolysis, vol. 6, No. 4, Jun. 1995, pp. 317-321.

Cheryl Holmes, et al., "Genetic Polymorphisms in Sepsis and Septic Shock," Chest, vol. 124, No. 3, Sep. 2003, pp. 1103-1115.

Roger C. Bone et al., "Definitions for Sepsis and Organ Failure and Guidelines for the Use of Innovative Therapies in Sepsis," The ACCP/SCCM Consensus Conference Committee: Chest (1992) 101:1644-55.

Ramakant Khazanie, "Elementary Statistics in a World of Applications" 3rd Ed., p. 400-401 Scott, Foresman/Little, Brown Higher Education (publisher), 1990.

* cited by examiner

SEPSIS SIRS 28 SURVIVAL BY PROTEIN C -1641 GENOTYPE

CPB SIRS: POST CPB HEMODYNAMICS (PROTEIN C -1641 GENOTYPES: 11 IS AA GENOTYPE, 12 IS AG GENOTYPE, 22 IS GG GENOTYPE)

POST-CPB SIRS POPULATION: OXYGENATION (PROTEIN C -1641 GENOTYPES: 11 IS AA GENOTYPE, 12 IS AG GENOTYPE, 22 IS GG GENOTYPE)

US 7,820,376 B2

PROTEIN C POLYMORPHISMS

RELATED APPLICATION DATA

This application relates to U.S. provisional application No. 60/383,128 filed May 28, 2002, which is incorporated herein by reference.

FIELD OF THE INVENTION

The field of the invention relates to the assessment or treatment of patients with an inflammatory condition.

BACKGROUND OF THE INVENTION

Protein C, when activated to form activated protein C (APC), plays a major role in three biological processes or conditions: coagulation, fibrinolysis and inflammation. Acute inflammatory states decrease levels of the free form of protein S, which decreases APC function because free protein S is an important co-factor for APC. Sepsis, acute inflammation and cytokines decrease thrombomodulin expression on endothelial cells resulting in decreased APC activity or levels. Septic shock also increases circulating levels of thrombomodulin, which is related to increased cleavage of endothelial cell thrombomodulin. Another mechanism for decreased APC function in sepsis is that endotoxin and cytokines, such as TNF-α, down-regulate endothelial cell protein C receptor (EPCR) expression, thereby decreasing action of APC. Severe septic states such as meningococcemia, also result in protein C consumption. Depressed protein C levels correlate with purpura, digital infarction and death in meningococcemia.

Protein C is altered in non-septic patients following cardiopulmonary bypass (CPB). Total protein C, APC and protein S decrease during CPB. Following aortic unclamping (reperfusion at the end of CPB) protein C is further activated so that the proportion of remaining non-activated protein C is greatly decreased. A decrease of protein C during and after CPB increases the risk of thrombosis, disseminated intravascular coagulation (DIC), organ ischemia and inflammation intra- and post-operatively. Patients who have less activated protein C generally have impaired recovery of cardiac function, consistent with the idea that lower levels of protein C increase the risk of microvascular thrombosis and myocardial ischemia. Aprotinin is a competitive inhibitor of APC, and is sometimes used in cardiac surgery and CPB. Aprotinin has been implicated as a cause of post-operative thrombotic complications after deep hypothermic circulatory arrest.

Septic and non-septic stimuli such as bacterial endotoxin and cardiopulmonary bypass (CPB), activate the coagulation system and trigger a systemic inflammatory response syndrome (SIRS). A decrease in protein C levels have been shown in patients with septic shock (GRIFFIN J H. et al. (1982) Blood 60:261-264; TAYLOR F B. et al. (1987) J. Clin. Invest. 79:918-925; HESSELVIK J F. et al. (1991) Thromb. Haemost. 65:126-129; FIJNVANDRAAT K. et al. (1995) Thromb. Haemost. 73(1):15-20), with severe infection (HESSELVIK J F. et al. (1991) Thromb. Haemost. 65:126-129) and after major surgery (BLAMEY S L. et al. (1985) Thromb. Haemost. 54:622-625). It has been suggested that this decrease is caused by a decrease in protein C transcription (SPEK C A. et al. J. Biological Chemistry (1995) 270(41): 24216-21 at 24221). It has also been demonstrated that endothelial pathways required for protein C activation are impaired in severe menigococcal sepsis (FAUST S N. et al. New Eng. J. Med. (2001) 345:408-416). Low protein C levels in sepsis patients are related to poor prognosis (YAN S B. and DHAINAUT J-F. Critical Care Medicine (2001) 29(7):S69-S74; FISHER C J. and YAN S B. Critical Care Medicine (2000) 28(9 Suppl):S49-S56; VERVLOET M G. et al. Semin Thromb Hemost. (1998) 24(1):33-44; LORENTE J A. et al. Chest (1993) 103(5):1536-42). Recombinant human activated protein C reduces mortality in patients having severe sepsis or septic shock (BERNARD G R. et al. New Eng. J. Med. (2001) 344:699-709). Thus protein C appears to play an important beneficial role in the systemic inflammatory response syndrome.

The human protein C gene maps to chromosome 2q13-q14 and extends over 11 kb. A representative *Homo sapiens* protein C gene sequence is listed in GenBank under accession number AF378903. Three single nucleotide polymorphisms (SNPs) have been identified in the 5' untranslated promoter region of the protein C gene and are characterized as −1654 C/T, −1641 A/G and −1476 A/T (according to the numbering scheme of FOSTER D C. et al. Proc Natl Acad Sci USA (1985) 82(14):4673-4677), or as −153C/T, −140A/G and +26A/T respectively by (MILLAR D S. et al. Hum. Genet. (2000) 106:646-653 at 651).

The genotype homozygous for −1654 C/−1641 G/−1476 T has been associated with reduced rates of transcription of the protein C gene as compared to the −1654 T/−1641 A/ −1476 A homozygous genotype (SCOPES D. et al. Blood Coagul. Fibrinolysis (1995) 6(4):317-321). Patients homozygous for the −1654 C/−1641 G/−1476 T genotype show a decrease of 22% in plasma protein C levels and protein C activity levels as compared to patients homozygous for the −1654 T/−1641 A/−1476 A genotype (SPEK C A. et al. Arteriosclerosis, Thrombosis, and Vascular Biology (1995) 15:214-218). The −1654 C/−1641 G haplotype has been associated with lower protein C concentrations in both homozygotes and heterozygotes as compared to −1654 T/−1641 A (AIACH M. et al. Arterioscler Thromb Vasc Biol. (1999) 19(6):1573-1576).

SUMMARY OF THE INVENTION

This invention is based in part on the surprising discovery that two of the protein C promoter polymorphisms characterized in the scientific literature as being associated with decreased protein C are associated with improved prognosis or patient outcome, in patients with an inflammatory condition. Further, various protein C polymorphisms are useful for patient screening, as an indication of patient outcome, or for prognosis for recovery from an inflammatory condition.

In accordance with one aspect of the invention, methods are provided for obtaining a prognosis for a patient having or at risk of developing an inflammatory condition, the method comprising determining a genotype including one or more polymorphism sites in the protein C gene for the patient, wherein said genotype is indicative of an ability of the patient to recover from an inflammatory condition.

The polymorphism site may correspond to position 2418 of SEQ ID NO.: 1 or a polymorphism site linked thereto. Alternatively, the polymorphism site corresponds to position 2418, 1386, 2583 or 3920 in SEQ ID NO: 1.

Genotype may also be determined at a combination of two or more polymorphism sites, the combination being selected from the group of positions corresponds to SEQ ID NO:1 consisting of:

5867 and 2405;
5867 and 4919;
5867 and 4956;
5867 and 6187;
5867 and 9534;

5867 and 12109;
4800 and 2405;
4800 and 4919;
4800 and 4956;
4800 and 6187;
4800 and 9534;
4800 and 12109;
9198 and 6379 and 2405;
9198 and 6379 and 4919;
9198 and 6379 and 4956;
9198 and 6379 and 6187;
9198 and 6379 and 9534; and
9198 and 6379 and 12109.

In accordance with another aspect of the invention, methods are provided for further comparing the genotype so determined with known genotypes, which are indicative of a prognosis for recovery from the same inflammatory condition as for the patient or another inflammatory condition.

The genotype of the patient may be indicative of a decreased likelihood of recovery from an inflammatory condition or indicative of a prognosis of severe cardiovascular or respiratory dysfunction in critically ill patients. Furthermore, such a genotype may be selected from the group of single polymorphism sites and combined polymorphism sites consisting of:
1386 T;
2418 A;
2583 A;
3920 T;
5867 A and 2405 T;
5867 A and 4919 A;
5867 A and 4956 T;
5867 A and 6187 C;
5867 A and 9534 T;
5867 A and 12109 T;
4800 G and 2405 T;
4800 G and 4919 A;
4800 G and 4956 T;
4800 G and 6187 C;
4800 G and 9534 T;
4800 G and 12109 T;
9198 A and 6379 G and 2405 T;
9198 A and 6379 G and 4919 A;
9198 A and 6379 G and 4956 T;
9198 A and 6379 G and 6187 C;
9198 A and 6379 G and 9534 T; and
9198 A and 6379 G and 12109 T.

The genotype of the patient may be indicative of an increased likelihood of recovery from an inflammatory condition or indicative of a prognosis of less severe cardiovascular or respiratory dysfunction in critically ill patients. Furthermore, such a genotype may be selected from the group of single polymorphism sites and combined polymorphism sites consisting of:
1386 C;
2418 G;
2583 T;
3920 C;
5867 G and 2405 C;
5867 G and 4919 G;
5867 G and 4956 C;
5867 G and 6187 T;
5867 G and 9534 C;
5867 G and 12109 C;
4800 C and 2405 C;
4800 C and 4919 G;
4800 C and 4956 C;
4800 C and 6187 T;
4800 C and 9534 C; and
4800 C and 12109 C.

In accordance with another aspect of the invention, methods are provided for identifying a polymorphism in a protein C gene sequence that correlates with patient prognosis. Where the method comprises obtaining protein C gene sequence information from a group of patients, identifying a site of at least one polymorphism in the protein C gene, determining genotypes at the site for individual patients in the group, determining an ability of individual patients in the group to recover from the inflammatory condition and correlating genotypes determined with patient abilities.

The correlation procedure may be repeated on a patient population of sufficient size to achieve a statistically significant correlation.

The methods may further comprise steps of obtaining protein C gene sequence of the patient or obtaining a nucleic acid sample from the patient. The determining of genotype may be performed on a nucleic acid sample from the patient.

Where the genotype of the patient corresponding to the nucleotide in position 2418, is adenine (A), the prognosis may be indicative of a decreased likelihood of recovery from an inflammatory condition or of severe cardiovascular or respiratory dysfunction in critically ill patients.

Where the genotype of the patient corresponding to the nucleotide in position 2418, is guanine (G), the prognosis may be indicative of a increased likelihood of recovery from an inflammatory condition or of less severe cardiovascular or respiratory dysfunction in critically ill patients.

The inflammatory condition may be selected from the group consisting of: sepsis, septicemia, pneumonia, septic shock, systemic inflammatory response syndrome (SIRS), Acute Respiratory Distress Syndrome (ARDS), acute lung injury, infection, pancreatitis, bacteremia, peritonitis, abdominal abscess, inflammation due to trauma, inflammation due to surgery, chronic inflammatory disease, ischemia, ischemia-reperfusion injury of an organ or tissue, tissue damage due to disease, tissue damage due to chemotherapy or radiotherapy, and reactions to ingested, inhaled, infused, injected, or delivered substances.

The determining of a genotype may comprise one or more of: restriction fragment length analysis; sequencing; hybridization; oligonucleotide ligation assay; ligation rolling circle amplification; 5' nuclease assay; polymerase proofreading methods; allele specific PCR; and reading sequence data.

In accordance with another aspect of the invention, there is provided a kit for determining a genotype at a defined nucleotide position within a polymorphism site in a protein C gene sequence from a patient to provide a prognosis of the patient's ability to recover from an inflammatory condition, the kit comprising, in a package a restriction enzyme capable of distinguishing alternate nucleotides at the polymorphism site or a labeled oligonucleotide having sufficient complementary to the polymorphism site and capable of distinguishing said alternate nucleotides.

The alternate nucleotides may correspond to position 2418 of SEQ ID NO: 1, position 8 of SEQ ID NO: 2 or to a polymorphism linked thereto. The alternate nucleotides may also correspond to one or more of positions 2418, 1386, 2583, and 3920 of SEQ ID NO: 1.

The kit comprising a restriction enzyme may also comprise an oligonucleotide or a set of oligonucleotides suitable to amplify a region surrounding the polymorphism site, a polymerization agent and instructions for using the kit to determine genotype.

In accordance with another aspect of the invention, methods are provided for determining patient prognosis in a patient having or at risk of developing an inflammatory condition, the method comprising detecting the identity of one or more polymorphisms in the protein C promoter region, wherein the identity of said one or more polymorphisms is indicative of the ability of the patient to recover from the inflammatory condition.

In accordance with another aspect of the invention, methods are provided for patient sreening, comprising the steps of (a) obtaining protein C gene sequence information from a patient, and (b) determining the identity of one or more polymorphisms in the promoter region, wherein the one or more polymorphisms may be indicative of the ability of a patient to recover from an inflammatory condition.

In accordance with another aspect of the invention methods are provided for patient screening whereby the method includes the steps of (a) selecting a patient based on risk of developing an inflammatory condition or having an inflammatory condition, (b) obtaining protein C gene sequence information from the patient and (c) detecting the identity of one or more polymorphisms in the protein C gene, wherein the polymorphism is indicative of the ability of a patient to recover from an inflammatory condition.

The above sequence positions refer to the sense strand of the protein C gene promoter region. It will be obvious to a person skilled in the art that analysis could be conducted on the anti-sense strand to determine patient outcome.

More severe patient outcome or prognosis may be correlated with higher protein C expression or conversely an indication of less severe patient outcome or prognosis may be correlated with lower protein C expression, which is the opposite of what would be expected.

DETAILED DESCRIPTION OF THE INVENTION

1. Definitions

Figure 1:
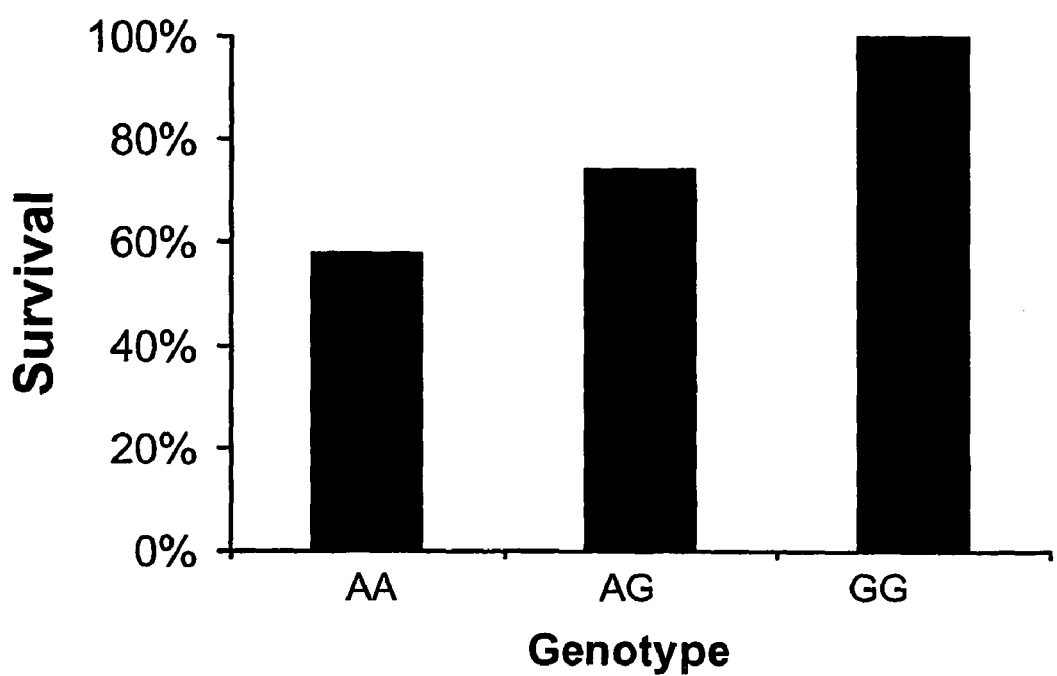
FIG. 1 shows a comparison of survival rates for patients in shock with those not in shock by genotype of protein C 2418.

In the description that follows, a number of terms are used extensively, the following definitions are provided to facilitate understanding of the invention.

"Genetic material" includes any nucleic acid and can be a deoxyribonucleotide or ribonucleotide polymer in either single or double-stranded form.

A "purine" is a heterocyclic organic compound containing fused pyrimidine and imidazole rings, and acts as the parent compound for purine bases, adenine (A) and guanine (G). "Nucleotides" are generally a purine (R) or pyrimidine (Y) base covalently linked to a pentose, usually ribose or deoxyribose, where the sugar carries one or more phosphate groups. Nucleic acids are generally a polymer of nucleotides joined by 3'5' phosphodiester linkages. As used herein "purine" is used to refer to the purine bases, A and G, and more broadly to include the nucleotide monomers, deoxyadenosine-5'-phosphate and deoxyguanosine-5'-phosphate, as components of a polynucleotide chain.

A "pyrimidine" is a single-ringed, organic base that forms nucleotide bases, cytosine (C), thymine (T) and uracil (U). As used herein "pyrimidine" is used to refer to the pyrimidine bases, C, T and U, and more broadly to include the pyrimidine nucleotide monomers that along with purine nucleotides are the components of a polynucleotide chain.

A "polymorphic site" or "polymorphism site" or "polymorphism" or "single nucleotide polymorphism site" (SNP site) as used herein is the locus or position with in a given sequence at which divergence occurs. Preferred polymorphic sites have at least two alleles, each occurring at frequency of greater than 1%, and more preferably greater than 10% or 20% of a selected population. Polymorphism sites may be at known positions within a nucleic acid sequence or may be determined to exist using the methods described herein.

The "promoter" region is 5' or upstream of the translation start site, in this case the translation start site is located at position 4062 of TABLE 1A (SEQ. ID NO: 1) and the transcription start site is located at position 2559 of TABLE 1A (SEQ. ID NO: 1).

Numerous other sites have been identified as polymorphisms in the protein C gene, where those polymorphisms are linked to the polymorphism at position 2418 of SEQ. ID NO: 1 and may therefore be indicative of patient prognosis. The following single polymorphism sites and combined polymorphism sites are linked to 2418 of SEQ. ID NO.: 1:

1386;
2583;
3920;
5867 and 2405;
5867 and 4919;
5867 and 4956;
5867 and 6187;
5867 and 9534;
5867 and 12109;
4800 and 2405;
4800 and 4919;
4800 and 4956;
4800 and 6187;
4800 and 9534;
4800 and 12109;
9198 and 6379 and 2405;
9198 and 6379 and 4919;
9198 and 6379 and 4956;
9198 and 6379 and 6187;
9198 and 6379 and 9534; and
9198 and 6379 and 12109.

It will be appreciated by a person of skill in the art that further linked single polymorphism sites and combined polymorphism sites could be determined. The haplotype of protein C can be created by assessing the SNP's of protein C in normal subjects using a program that has an expectation maximization algorithm (i.e. PHASE). A constructed haplotype of protein C may be used to find combinations of SNP's that are in total linkage disequilibrium (LD) with 2418. Therefore, the haplotype of an individual could be determined by genotyping other SNP's that are in total LD with 2418. Linked single polymorphism sites or combined polymorphism sites may also be genotyped for assessing patient prognosis.

The following genotypes for single polymorphism sites and combined polymorphism sites may indicative of a decreased likelihood of recovery from an inflammatory condition or indicative of severe cardiovascular or respiratory dysfunction in critically ill patients:
1386 T;
2583 A;
3920 T;
5867 A and 2405 T;
5867 A and 4919 A;
5867 A and 4956 T;
5867 A and 6187 C;
5867 A and 9534 T;
5867 A and 12109 T;
4800 G and 2405 T;
4800 G and 4919 A;
4800 G and 4956 T;
4800 G and 6187 C;
4800 G and 9534 T;
4800 G and 12109 T;
9198 A and 6379 G and 2405 T;
9198 A and 6379 G and 4919 A;
9198 A and 6379 G and 4956 T;
9198 A and 6379 G and 6187 C;
9198 A and 6379 G and 9534 T; and
9198 A and 6379 G and 12109 T.

Whereas the following genotypes for single polymorphism sites and combined polymorphism sites may indicative of a increased likelihood of recovery from an inflammatory condition or indicative of less severe cardiovascular or respiratory dysfunction in critically ill patients:
1386 C;
2583 T;
3920 C;
5867 G and 2405 C;
5867 G and 4919 G;
5867 G and 4956 C;
5867 G and 6187 T;
5867 G and 9534 C;
5867 G and 12109; C
4800 C and 2405 C;
4800 C and 4919 G;
4800 C and 4956 C;
4800 C and 6187 T;
4800 C and 9534 C; and
4800 C and 12109 C.

It will be appreciated by a person of skill in the art, that the numerical designations of the positions of polymorphisms within a sequence are relative to the specific sequence. Also the same positions may be assigned different numerical designations depending on the way in which the sequence is numbered and the sequence chosen, as illustrated by the alternative numbering of equivalent polymorphisms in Foster et al. and Millar et al. above. Furthermore, sequence variations within the population, such as insertions or deletions, may change the relative position and subsequently the numerical designations of particular nucleotides at and around a polymorphism site.

TABLE 1A below is representative of a *Homo sapiens* protein C gene sequence and comprises a sequence as listed in GenBank under accession number AF378903. The SNP's described as −1654 C/T, −1641 A/G and −1476 A/T using the numbering system of Foster et al. correspond to 2405, 2418 and 2583 respectively in TABLE 1A (SEQ ID NO: 1). Polymorphism sites shown below in TABLE 1A are represented by a capital N at the apex of an open triangle. The N is used to indicate that variation in genotype is possible at those positions within a population. The 2418 polymorphism is represented by an N which indicates that the nucleotide at that position may be an a, t, u, g or c. However, the genotype at position 2418 is most commonly an a or g (purine) nucleotide.

TABLE 1A

```
   1 gctctctaac tcacagcgag ctcgctgccc aaagtcctgc
     tccgggggct tcctgggtgg 61 acctgaccgc gttcgggtgc acgtggggcg actcacacct
     gacaagtaaa gcgggtgagg 121 ccgcgcctgt gaagggcgcc tggctcctcc gcaggacggt
     gcggcgcggc gccccggct 181 ggaaccaggt gtaactgcag agaccctggg atcgcaggaa
     cggctggcgg caggactgtc 241 cctacctcga gaaggtgacg gggtttcctg cgctgccagc
     cgatgaggcg gccgtgacgc 301 agcccgccgt gcagagtccc cgtcggccga caggcgtgca
     gagctctgca gaggaccctt 361 ccgccctctg ggcagcctgc caagccgtgg cacccccaac
     ccccagcact gggcacttgg 421 gagcattgca gccgccctgg ctcgtaccgg tgccggtgct
     ttgggcacct gggctggttt 481 ggacatgggt gccccgggca gagtccattt atgcaggtca
     gaatcagtgt gtggagcctg 541 catagacttg ccctggagcg gctgcctgtg ctggggtggg
     gaggagtaga gggcgagaag 601 ttggtgggga agggaagcgg cgccaaaaga atacccacaa
     catcttgcac ctggaaggca 661 aagcagaggg cagtgatctc tgcagacttg cggggggcgac
     gcctgaagca aacagggaca 721 tacaagctgg tgccttctgt ggttgtgcat ggggtcttca
     tgcttcctgt ctgagttccc 781 agaagcttgt ctctgctttt ctaggcagct gccacagcct
     gtcacaaaca gctcctggtt 841 ctccacttct catagtctcg atttcaaaat ccattgcctc
     accctccacc tcctctccac 901 ctccacccct cctagcacct cctgactgct tgtgttctgt
     gtctccccac tgtctcccaa 961 cctggggtgg ggttgggggg gatgtctttc ctcctgtctg
     ctctttgatg tccagctgaa 1021 gtgtcacctc ctacaggcag cctcccctgg ctatgccagc
     ttgtactgat tgccctctcc 1081 tctgaattct gtaagcattt cctatgtgta cctgcccctg
     ggcaaggtgg gcctgacttg 1141 ttagagtgtt agagttttac cctgttcctc taggagggcc
     tggtaccacc acagcccagc 1201 atggtgtggt gcctcagcag gaggcatctg gttacaatca
     acacaagctg ttccagccaa 1261 tttaaagaaa cttcaggagg aatagggttt taggagggca
     tggggaccct cctgcacccg 1321 aagccaggat gtgccaccaa tcataaggag gcaggggcct
     ccttccgctg ctccctggga 1381 ctctcNaggt gtccgtggcc tcagcccccc tctgcacacc
          A
     tgcatcttcc ttctcatcag
```

TABLE 1A-continued

```
1441 cttcctctgc tttaagcgta aacatggatg cccaggacct
     ggcctcaatc ttccgagtct 1501 ggtacttatg gtgtactgac agtgtgagac cctactcctc
     tgatcaatcc cctgggttgg 1561 tgacttccct gtgcaatcaa tggaagccag cgaggcaggg
     tcacatgccc cgtttagagg 1621 tgcagacttg gagaaggaac gtgggcaagt cttcccagga
     acaggtaggg cagggaggaa 1681 aggggggcat ctctggtgca gcccggttcg gagcaggaag
     acgcttaata aatgctgata 1741 gactgcagga cacaggcaaa ggtgctgagc tggacccttt
     atttctgccc ttctcccttc 1801 tggcaccccg gccaggaaat tgctgcagcc tttctggaat
     cccgttcatt tttcttactg 1861 gtccacaaaa ggggccaaat ggaagcagca agacctgagt
     tcaaattaaa tctgccaact 1921 accagctcag tgaatctggg cgagtaacac aaaacttgag
     tgtccttacc tgaaaaatag 1981 aggttagagg gatgctatgt gccattgtgt gtgtgtgttg
     ggggtgggga ttgggggtga 2041 tttgtgagca attggaggtg agggtggagc ccagtgccca
     gcacctatgc actgggacc 2101 caaaaaggag catcttctca tgattttatg tatcagaaat
     tgggatggca tgtcattggg 2161 acagcgtctt ttttcttgta tggtggcaca taaatacatg
     tgtcttataa ttaatggtat 2221 tttagatttg acgaaatatg gaatattacc tgttgtgctg
     atcttgggca aactataata 2281 tctctgggca aaaatgtccc catctgaaaa acagggacaa
     cgttcctccc tcagccagcc 2341 actatggggc taaaatgaga ccacatctgt caagggtttt
     gccctcacct ccctccctgc 2401 tggaNggcat ccttggtNgg cagaggtggg cttcgggcag
         Δ        Δ
     aacaagccgt gctgagctag 2461 gaccaggagt gctagtgcca ctgtttgtct atggagaggg
     aggcctcagt gctgagggcc 2521 aagcaaatat ttgtggttat ggattaactc gaactccagg
     ctgtcatggc ggcaggacgg 2581 cgNacttgca gtatctccac gacccgcccc tgtgagtccc
       Δ
     cctccaggca ggtctatgag 2641 gggtgtggag ggagggctgc ccccgggaga agagagctag
     gtggtgatga gggctgaatc 2701 ctccagccag ggtgctcaac aagcctgagc ttggggtaaa
     aggacacaag gccctccaca 2761 ggccaggcct ggcagccaca gtctcaggtc cctttgccat
     gcgcctccct ctttccaggc 2821 caagggtccc cagggcccag ggccattcca acagacagtt
     tggagcccag gaccctccat 2881 tctccccacc ccacttccac ctttgggggt gtcggatttg
     aacaaatctc agaagcggcc 2941 tcagagggag tcggcaagaa tggagagcag ggtccggtag
     ggtgtgcaga gggccacgtg 3001 gcctatccac tggggagggt tccttgatct ctggccacca
     gggctatctc tgtggcctttt 3061 tggagcacct ggtggtttgg ggcaggggtt gaatttccag
     gcctaaaacc acacaggcct 3121 ggccttgagt cctggctctg cgagtaatgc atggatgtaa
     acatggagac ccaggacctt 3181 gcctcagtct tccgagtctg gtgcctgcag tgtactgatg
     gtgtgagacc ctactcctgg 3241 aggatggggg acagaatctg atcgatcccc tgggttggtg
     acttccctgt gcaatcaacg 3301 gagaccagca agggttggat ttttaataaa ccacttaact
     cctccgagtc tcagtttccc 3361 cctctatgaa atggggttga cagcattaat aactacctct
     tgggtggttg tgagccttaa 3421 ctgaagtcat aatatctcat gtttactgag catgagctat
     gtgcaaagcc tgttttgaga 3481 gctttatgtg gactaactcc tttaattctc acaacaccct
     ttaaggcaca gatacaccac 3541 gttattccat ccattttaca aatgaggaaa ctgaggcatg
     gagcagttaa gcatcttgcc 3601 caacattgcc ctccagtaag tgctggagct ggaatttgca
     ccgtgcagtc tggcttcatg 3661 gcctgccctg tgaatcctgt aaaaattgtt tgaaagacac
     catgagtgtc caatcaacgt 3721 tagctaatat tctcagccca gtcatcagac cggcagaggc
     agccacccca ctgtccccag 3781 ggaggacaca aacatcctgg caccctctcc actgcattct
     ggagctgctt tctaggcagg 3841 cagtgtgagc tcagccccac gtagagcggg cagccgagcc
     cttctgaggc tatgtctcta 3901 gcgaacaagg accctcaatN ccagcttccg ccctgacggc
                      Δ
     cagcacacag ggacagccct 3961 ttcattccgc ttccacctgg gggtgcaggc agagcagcag
     cggggggtagg cactgcccgg 4021 agctcagaag tcctcctcag acaggtgcca gtgcctccag
     aatgtgccag ctcacaagcc 4081 tcctgctgtt cgtggccacc tggggaattt ccggcacacc
     agctcctctt ggtaaggcca 4141 ccccacccct accccgggac ccttgtggcc tctacaaggc
     ctggtggcat ctgcccaggc 4201 cttcacagct tccaccatct ctctgagccc tgggtgaggt
     gagggcaga tgggaatggc 4261 aggaatcaac tgacaagtcc caggtaggcc agctgccaga
     gtgccacaca ggggctgcca 4321 gggcaggcat gcgtgatggc agggagcccc gcgatgacct
     cctaaagctc ctcctccac 4381 acggggatgg tcagagagtc ccctgggcct tccctctcca
     cccactcact ccctcaactg 4441 tgaagacccc aggccaggc taccgtccac actatccagc
     acagcctccc ctactcaaat 4501 gcacactggc ctcacggctg ccctgcccca accccttttcc
     tggtctccac agccaacggg
```

TABLE 1A-continued

```
4561 aggaggccat gattcttggg gaggtccgca ggacacatgg
     gcccctaaag ccacaccagg 4621 ctgttggttt catttgtgcc tttatagagc tgtttatctg
     cttgggacct gcacctccac 4681 cctttcccaa ggtgccctca gctcaggcat accctcctct
     aggatgcctt ttcccccatc 4741 ccttcttgct cacaccccca acttgatctc tccctcctaa
     ctgtgccctg cacccaagaN
                        Δ

4801 agacacttca cagagcccag gagacacctg gggacccttc
     ctgggtgata ggtctgtcta 4861 tcctccaggt gtccctgccc aaggggagaa gcatgggaa
     tacttggttg ggggaggaNa
                        Δ

4921 ggaagactgg ggggatgtgt caagatgggg ctgcaNgtgg
                                         Δ
     tgtactggca aaagagtgag 4981 aggatttaac ttggcagcct ttacagcagc agccagggct
     tgagtactta tctctgggcc 5041 agggactgta ttggatgttt tacatgacgg tctcatcccc
     atgttttttgg atgagtaaat 5101 tgaaccttag aaaggtaaag acactggctc aaggtcacac
     agagatcggg gtggggttca 5161 cagggaggcc tgtccatctc agagcaaggc ttcgtcctcc
     aactgccatc tgcttcctgg 5221 ggaggaaaag agcagaggac ccctgcgcca agccatgacc
     tagaattaga atgagtcttg 5281 aggggcggga gacaagacct tcccaggctc tcccagctct
     gcttcctcag acccctcat 5341 ggccccagcc cctcttaggc ccctccacca aggtgagctc
     cccctccctc caaaaccaga 5401 ctcagtgttc tccagcagcg agcgtgccca ccaggtgctg
     cggatccgca aacgtgccaa 5461 ctccttcctg gaggagctcc gtcacagcag cctggagcgg
     gagtgcatag aggagatctg 5521 tgacttcgag gaggccaagg aaattttcca aaatgtggat
     gacacagtaa ggccaccatg 5581 ggtccagagg atgaggctca ggggcgagct ggtaaccagc
     aggggcctcg aggagcaggt 5641 ggggactcaa tgctgaggcc ctcttaggag ttgtgggggt
     ggctgagtgg agcgattagg 5701 atgctggccc tatgatgtcg gccaggcaca tgtgactgca
     agaaacagaa ttcaggaaga 5761 agctccagga aagagtgtgg ggtgaccctta ggtggggact
     cccaccagcc acagtgtagg 5821 tggttcagtc caccctccag ccactgctga gcaccactgc
     ctccccNtcc cacctcacaa
          Δ

5881 agagggggacc taaagaccac cctgcttcca cccatgcctc
     tgctgatcag ggtgtgtgtg 5941 tgaccgaaac tcacttctgt ccacataaaa tcgctcactc
     tgtgcctcac atcaaaggga 6001 gaaaatctga ttgttcaggg ggtcggaaga cagggtctgt
     gtcctatttg tctaagggtc
```

```
6061 agagtccttt ggagccccca gagtcctgtg gacgtggccc
     taggtagtag ggtgagcttg 6121 gtaacgggc tggcttcctg agacaaggct cagacccgct
     ctgtccctgg ggatcgcttc 6181 agccacNagg acctgaaaat tgtgcacggc ctgggccccc
          Δ
     ttccaaggca tccagggatg 6241 ctttccagtg gaggctttca gggcaggaga ccctctggcc
     tgcaccctct cttgccctca 6301 gcctccacct ccttgactgg acccccatct ggacctccat
     ccccaccacc tctttcccca 6361 gtggcctccc tggcagacNc cacagtgact ttctgcaggc
                     Δ
     acatatctga tcacatcaag 6421 tccccaccgt gctcccacct cacccatggt ctctcagccc
     cagcaggcct tggctggcct 6481 ctctgatgga gcaggcatca ggcacaggcc gtgggtctca
     acgtgggctg ggtggtcctg 6541 gaccagcagc agccgccgca gcagcaaccc tggtacctgg
     ttaggaacgc agaccctctg 6601 cccccatcct cccaactctg aaaaacactg gcttagggaa
     aggcgcgatg ctcaggggtc 6661 ccccaaagcc cgcaggcaga gggagtgatg ggactggaag
     gaggccgagt gacttggtga 6721 gggattcggg tcccttgcat gccagaggct gctgtgggag
     cggacagtcg cgagagcagc 6781 actgcagctg catgggagaa gggtgttgct ccagggacgt
     gggatggagg ctgggcgcgg 6841 gcgggtggcg ctggagggcg gggaggggc agggagcacc
     agctcctagc agcaacgac 6901 catcggggcgt cgatccctgt ttgtctggaa gccctcccct
     cccctgcccg ctcacccgct 6961 gccctgcccc acccgggcgc gccccctccg cacaccggct
     gcaggagcct gacgctgccc 7021 gctctctccg cagctggcct tctggtccaa gcacgtcggt
     gagtgcgttc tagatccccg 7081 gctggactac cggcgcccgc gcccctcggg atctctggcc
     gctgaccccc taccccgcct 7141 tgtgtcgcag acgtgacca gtgcttggtc ttgcccttgg
     agcacccgtg cgccagcctg 7201 tgctgcgggc acggcacgtg catcgacggc atcggcagct
     tcagctgcga ctgccgcagc 7261 ggctgggagg gccgcttctg ccagcgcggt gaggggaga
     ggtggatgct ggcgggcggc 7321 ggggcggggc tgggccgggt tggggcgcgc ggcaccagca
     ccagctgccc gcgccctccc 7381 ctgcccgcag aggtgagctt cctcaattgc tcgctggaca
     acggcggctg cacgcattac 7441 tgcctagagg aggtgggctg gcggcgctgt agctgtgcgc
     ctggctacaa gctggggggac 7501 gacctcctgc agtgtcaccc cgcaggtgag aagcccccaa
     tacatcgccc aggaatcacg
```

TABLE 1A-continued

```
7561  ctgggtgcgg ggtgggcagg ccccctgacgg ggcgcggcgc
      gggggggctca ggagggtttc 7621  tagggaggga gcgaggaaca gagttgagcc ttggggcagc
      ggcagacgcg ccccaacacc 7681  ggggccactg ttagcgcaat cagcccggga gctgggcgcg
      ccctccgctt tccctgcttc 7741  cttctcttcct ggcgtccccg ccttcctccg ggcgcccct
      gcgcacctgg ggccacctcc 7801  tggagcgcaa gcccagtggt ggctccgctc cccagtctga
      gcgtatctgg ggcgaggcgt 7861  gcagcgtcct cctccatgta gcctggctgc gttttctct
      gacgttgtcc ggcgtgcatc 7921  gcatttccct ctttacccccc ttgcttcctt gaggagagaa
      cagaatcccg attctgcctt 7981  cttctatatt ttccttttta tgcattttaa tcaaatttat
      atatgtatga aactttaaaa 8041  atcagagttt tacaactctt acatttcagc atgctgttcc
      ttggcatggg tcctttttc 8101  attcattttc attaaaaggt ggacccttt aatgtggaaa
      ttcctatctt ctgcctctag 8161  ggacatttat cacttattc ttctacaatc tccccttac
      ttcctctatt ttctctttct 8221  ggacctccca ttattcagac ctctttcctc tagttttatt
      gtctcttcta tttccccatct 8281  ctttgacttt gtgtttcctt tcagggaact ttccttttt
      tctttttttt tgagatggag 8341  tttcactctt gttgtcccag gctggagtgc aatgacgtga
      tctcagctca ccacaacctc 8401  cgcctcctgg attcaagcga ttctcctgcc gcagcctccc
      gagtagctgg gattacaggc 8461  atgcgccacc acgcccagct aatttttgtgt ttttagtaga
      gaagggggttt tccgtgttg 8521  gtcaagctgg tcttgaactc ctgacctcag gtgatccacc
      tgccttggcc tcctaaagtg 8581  ctgggattac aggcgtgagc caccgcgccc agcctctttc
      agggaacttt ctacaacttt 8641  ataattcaat tcttctgcag aaaaaaattt ttggccaggc
      tcagtagctc agaccaataa 8701  ttccagcact ttgagaggct gaggtgggag gattgcttga
      gcttgggagt ttgagactag 8761  cctgggcaac acagtgagac cctgtctcta ttttaaaaa
      aagtaaaaaa agatctaaaa 8821  atttaactt ttatttgaa ataattagat atttccagga
      agctgcaaag aaatgcctgg 8881  tgggcctgtt ggcctgtggg tttcctgcaa ggccgtggga
      aggccctgtc attggcagaa 8941  ccccagatcg tgagggcttt cctttaggc tgctttctaa
      gaggactcct ccaagctctt 9001  ggaggatgga agacgctcac ccatggtgtt cggcccctca
      gagcagggtg gggcagggga 9061  gctggtgcct gtgcaggctg tggacatttg catgactccc
      tgtggtcagc taagagcacc
```

```
9121   actccttcct gaagcggggc ctgaagtccc tagtcagagc
       ctctggttca ccttctgcag 9181   gcagggagag gggagtcNag tcagtgagga gggctttcgc
                       Δ
       agtttctctt acaaactctc 9241   aacatgccct cccacctgca ctgccttcct ggaagcccca
       cagcctccta tggttccgtg 9301   gtccagtcct tcagcttctg ggcgccccca tcacgggctg
       agattttgc tttccagtct 9361   gccaagtcag ttactgtgtc catccatctg ctgtcagctt
       ctggaattgt tgctgttgtg 9421   cccttttccat tcttttgtta tgatgcagct cccctgctga
       cgacgtccca ttgctctttt 9481   aagtctagat atctggactg ggcattcaag gcccattttg
       agcagagtcg ggcNgacctt
                          Δ

9541   tcagccctca gttctccatg gagtatgcgc tctcttcttg
       gcaggaggc ctcacaaaca 9601   tgccatgcct attgtaggag ctctccaaga atgctcacct
       ccttctccct gtaattcctt 9661   tcctctgtga ggagctcagc agcatcccat tatgagacct
       tactaatccc agggatcacc 9721   cccaacagcc ctgggtaca atgagctttt aagaagttta
       accacctatg taaggagaca 9781   caggcagtgg gcgatgctgc ctggcctgac tcttgccatt
       gggtggtact gtttgttgac 9841   tgactgactg actgactgga gggggtttgt aatttgtatc
       tcagggatta cccccaacag 9901   ccctgggta caatgagcct tcaagaagtt taacaaccta
       tgtaaggaca cacagccagt 9961   gggtgatgct gcctggtctg actcttgcca ttcagtggca
       ctgtttgttg actgactgac 10021  tgactgactg gctgactgga gggggttcat agctaatatt
       aatggagtgg tctaagtatc 10081  attggttcct tgaaccctgc actgtggcaa agtggcccac
       aggctggagg aggaccaaga 10141  caggagggca gtctcgggag gagtgcctgg caggcccctc
       accacctctg cctacctcag 10201  tgaagttccc ttgtgggagg ccctggaagc ggatggagaa
       gaagcgcagt cacctgaaac 10261  gagacacaga agaccaagaa gaccaagtag atccgcggct
       cattgatggg aagatgacca 10321  ggcggggaga cagcccctgg caggtgggag gcgaggcagc
       accggctgct cacgtgctgg 10381  gtccgggatc actgagtcca tcctggcagc tatgctcagg
       gtgcagaaac cgagagggaa 10441  gcgctgccat tgcgtttggg ggatgatgaa ggtgggggat
       gcttcaggga aagatggacg 10501  caacctgagg ggagaggagc agccagggtg ggtgagggga
       ggggcatggg ggcatggagg 10561  ggtctgcagg agggagggtt acagtttcta aaaagagctg
       gaaagacact gctctgctgg 10621  cgggattta ggcagaagcc ctgctgatgg gagagggcta
       ggaggagggg ccgggcctga
```

TABLE 1A-continued

```
10681 gtacccctcc agcctccaca tgggaactga cacttactgg
     gttcccctct ctgccaggca 10741 tgggggagat aggaaccaac aagtgggagt atttgccctg
     gggactcaga ctctgcaagg 10801 gtcaggaccc caaagacccg gcagcccagt gggaccacag
     ccaggacggc ccttcaagat 10861 aggggctgag ggaggcccaa ggggaacatc caggcagcct
     gggggccaca aagtcttcct 10921 ggaagacaca aggcctggcc aagcctctaa ggatgagagg
     agctcgctgg gcgatgttgg 10981 gtgtggctga gggtgactga aacagtatga acagtgcagg
     aacagcatgg gcaaaggcag 11041 gaagacaccc tgggacaggc tgacactgta aaatgggcaa
     aaatagaaaa cgccagaaag 11101 ggcctaagcc tatgcccata tgaccaggga acccaggaaa
     gtgcatatga aacccaggtg 11161 ccctggactg gaggctgtca ggaggcagcc ctgtgatgtc
     atcatcccac cccattccag 11221 gtggtcctgc tggactcaaa gaagaagctg gcctgcgggg
     cagtgctcat ccacccctcc 11281 tgggtgctga cagcggccca ctgcatggat gagtccaaga
     agctccttgt caggcttggt 11341 atgggctgga gccaggcaga agggggctgc cagaggcctg
     ggtaggggga ccaggcaggc 11401 tgttcaggtt tgggggaccc cgctccccag gtgcttaagc
     aagaggcttc ttgagctcca 11461 cagaaggtgt ttgggggggaa gaggcctatg tgcccccacc
     ctgcccaccc atgtacaccc 11521 agtatttgc agtagggggt tctctggtgc cctcttcgaa
     tctgggcaca ggtacctgca 11581 cacacatgtt tgtgaggggc tacacagacc ttcacctctc
     cactcccact catgaggagc 11641 aggctgtgtg ggcctcagca ccccttgggtg cagagaccag
     caaggcctgg cctcagggct 11701 gtgcctccca cagactgaca gggatggagc tgtacagagg
     gagccctagc atctgccaaa 11761 gccacaagct gcttccctag caggctgggg gcacctatgc
     attggccccg atctatggca 11821 atttctggag gggggtctg gctcaactct ttatgccaaa
     aagaaggcaa agcatattga 11881 gaaaggccaa attcacattt cctacagcat aatctatggc
     cagtggcccc ccgtgggcct 11941 tggcttagaa ttccaggtc tcttcccag ggaaccatca
     gtctgactg agaggacctt 12001 ctctctcagg tgggacccgg ccctgtcctc cctggcagtg
     ccgtgttctg ggggtcctcc 12061 tctctgggtc tcactgcccc tggggtctct ccagctacct
     ttgctccaNg ttcctttgtg
              Δ

12121 gctctggtct gtgtctgggg tttccagggg tctcgggctt
     ccctgctgcc cattccttct 12181 ctggtctcac ggctccgtga ctcctgaaaa ccaaccagca
     tcctacccct ttgggattga
```

TABLE 1A-continued

```
12241 cacctgttgg ccactccttc tggcaggaaa agtcaccgtt
     gataggttc cacggcatag 12301 acaggtggct ccgcgccagt gcctgggacg tgtgggtgca
     cagtctccgg gtgaaccttc 12361 ttcaggccct ctgcccaggc ctgcaggggc acagcagtgg
     gtgggcctca ggaaagtgcc 12421 actggggaga ggctccccgc agcccactct gactgtgccc
     tctgcccctgc aggagagtat 12481 gacctgcggc gctgggagaa gtgggagctg acctggaca
     tcaaggaggt cttcgtccac 12541 cccaactaca gcaagagcac caccgacaat gacatcgcac
     tgctgcacct ggcccagccc 12601 gccaccctct cgcagaccat agtgcccatc tgcctcccgg
     acagcggcct tgcagagcgc 12661 gagctcaatc aggccggcca ggagaccctc gtgacgggct
     ggggctacca cagcagccga 12721 gagaaggagg ccaagagaaa ccgcaccttc gtcctcaact
     tcatcaagat tcccgtggtc 12781 ccgcacaatg agtgcagcga ggtcatgagc aacatggtgt
     ctgagaacat gctgtgtgcg 12841 ggcatcctcg ggaccggca ggatgcctgc gagggcgaca
     gtgggggcc catggtcgcc 12901 tccttccacg gcacctggtt cctggtgggc ctggtgagct
     ggggtgaggg ctgtgggctc 12961 cttcacaact acggcgttta caccaaagtc agccgctacc
     tcgactggat ccatgggcac 13021 atcagagaca aggaagcccc ccagaagagc tgggcacctt
     agcgaccctc cctgcagggc 13081 tgggcttttg catggcaatg gatgggacat taaagggaca
     tgtaacaagc acaccggcct 13141 gctgttctgt ccttccatcc ctcttttggg ctcttctgga
     gggaagtaac atttactgag 13201 cacctgttgt atgtcacatg ccttatgaat agaatcttaa
     ctcctagagc aactctgtgg 13261 ggtggggagg agcagatcca agttttgcgg ggtctaaagc
     tgtgtgtgtt gagggggata 13321 ctctgtttat gaaaaagaat aaaaaacaca accacgaagc
     cactagagcc ttttccaggg 13381 ctttgggaag agcctgtgca agccggggat gctgaaggtg
     aggcttgacc agctttccag 13441 ctagcccagc tatgaggtag acatgtttag ctcatatcac
     agaggaggaa actgaggggt 13501 ctgaaaggtt tacatggtgg agccaggatt caaatctagg
     tctgactcca aaacccaggt 13561 gcttttttct gttctccact gtcctggagg acagctgttt
     cgacggtgct cagtgtggag 13621 gccactatta gctctgtagg gaagcagcca gagacccaga
     aagtgttggt tcagcccaga 13681 atgagctcac agtgtcgcgg gggaagctgt ttaagaacaa
     tgttacacca tcatgaacag
```

TABLE 1A-continued

```
13741 cagtaagaaa gaggctctgg cttaacctgg cctgataggc
      ctaattgaat gagacagaaa 13801 taagtcaagg atgctctgat ttgaaatcat gaagtacctg
      atgaaaagaa atggtggtga 13861 gataaagctg
```

Table 1B

The sequences shown in TABLE 1B, are sequence fragments taken from the Protein C sequence shown in TABLE 1A above. Furthermore, SEQ ID NO.: 2 corresponds to the sequence underlined in TABLE 1A above. The nucleotide N, at position 8 in SEQ ID NO.: 2 corresponds to the nucleotide found at position 2418 of SEQ ID NO.: 1. In all of the Sequences found in TABLE 2B below the polymorphism represented by an N may substituted by an a, t, u, g or c. Furthermore, bold and underlined nucleotides represented by N in SEQ ID NOs.: 3-11 in TABLE 2B, all correspond to the nucleotide found at position 2418 of SEQ ID NO.: 1. Due to the potential variability in protein C sequence, the sequence motifs below may be useful in identifying protein C sequences from a patient that are suitable for genotype determination. For Example, patient sequences that form alignments with the below motifs (SEQ ID NO.: 3-11) may indicate that the patient sequence is a protein C sequence and that the bold and underlined N corresponds to the polymorphism at position 2418 of SEQ ID NO.: 1 and is therefore suitable for genotype determination. A similar strategy may be applied to the other polymorphism sites identified herein.

| SEQ ID. NO. | SEQUENCE |
|---|---|
| SEQ ID. NO. 2 | ccttggtNgg cagaggtggg |
| SEQ ID. NO. 3 | tggaNggcat ccttggtNgg |
| SEQ ID. NO. 4 | Nggcagaggt gggcttcggg |
| SEQ ID. NO. 5 | Nggcagaggt gggcttcggg cagaacaagc |
| SEQ ID. NO. 6 | gctggaNggc atccttggtN |
| SEQ ID. NO. 7 | ctccctccct gctggaNggc atccttggtN |
| SEQ ID. NO. 8 | ttgccctcac ctccctccct gctggaNggc atccttggtN |
| SEQ ID. NO. 9 | caagggtttt gccctcacct ccctccctgc tggaNggcat ccttggtNgg cagaggtggg cttcgggcag aacaagccgt gctgagctag |
| SEQ ID. NO. 10 | ccttggtNgg cagagg |
| SEQ ID. NO. 11 | cttggtNggc ag |

An "allele" is defined as any one or more alternative forms of a given gene. In a diploid cell or organism the members of an allelic pair (i.e. the two alleles of a given gene) occupy corresponding positions (loci) on a pair of homologous chromosomes and if these alleles are genetically identical the cell or organism is said to be "homozygous", but if genetically different the cell or organism is said to be "heterozygous" with respect to the particular gene.

A "gene" is an ordered sequence of nucleotides located in a particular position on a particular chromosome that encodes a specific functional product and may include untranslated and untranscribed sequences in proximity to the coding regions. Such non-coding sequences may contain regulatory sequences needed for transcription and translation of the sequence or introns etc.

A "genotype" is defined as the genetic constitution of an organism, usually in respect to one gene or a few genes or a region of a gene relevant to a particular context (i.e. the genetic loci responsible for a particular phenotype).

A "phenotype" is defined as the observable characters of an organism.

A "single nucleotide polymorphism" (SNP) occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations). A single nucleotide polymorphism usually arises due to substitution of one nucleotide for another at the polymorphic site. A "transition" is the replacement of one purine by another purine or one pyrimidine by another pyrimidine. A "transversion" is the replacement of a purine by a pyrimidine or vice versa. Single nucleotide polymorphisms can also arise from a deletion of a nucleotide or an insertion of a nucleotide relative to a reference allele. Furthermore, it would be appreciated by a person of skill in the art, that an insertion or deletion within a given sequence could alter the relative position and therefore the position number of another polymorphism within the sequence.

A "systemic inflammatory response syndrome" or (SIRS) is defined as including both septic (i.e. sepsis or septic shock) and non-septic systemic inflammatory response (i.e. post operative). "SIRS" is further defined according to ACCP (American College of Chest Physicians) guidelines as the presence of two or more of A) temperature>38° C. or <36° C., B) heart rate>90 beats per minute, C) respiratory rate>20 breaths per minute, and D) white blood cell count>12,000 per mm3 or <4,000 mm3. In the following description, the presence of two, three, or four of the "SIRS" criteria were scored each day over the 28 day observation period.

"Sepsis" is defined as the presence of at least two "SIRS" criteria and known or suspected source of infection. Septic shock was defined as sepsis plus one new organ failure by Brussels criteria plus need for vasopressor medication.

Patient outcome or prognosis as used herein refers the ability of a patient to recover from an inflammatory condition. An inflammatory condition, may be selected from the group consisting of: sepsis, septicemia, pneumonia, septic shock, systemic inflammatory response syndrome (SIRS), Acute Respiratory Distress Syndrome (ARDS), acute lung injury, infection, pancreatitis, bacteremia, peritonitis, abdominal abscess, inflammation due to trauma, inflammation due to surgery, chronic inflammatory disease, ischemia, ischemia-reperfusion injury of an organ or tissue, tissue damage due to disease, tissue damage due to chemotherapy or radiotherapy, and reactions to ingested, inhaled, infused, injected, or delivered substances.

Assessing patient outcome or prognosis may be accomplished by various methods. For Example, an "APACHE II" score is defined as A̲cute P̲hysiology A̲nd C̲hronic H̲ealth Evaluation and herein was calculated on a daily basis from raw clinical and laboratory variables. Vincent et al. (Vincent J L. Ferreira F. Moreno R. *Scoring systems for assessing organ dysfunction and survival*. Critical Care Clinics. 16:353-366, 2000) summarize APACHE score as follows "First developed in 1981 by Knaus et al., the APACHE score has become the most commonly used survival prediction model in ICUs worldwide. The APACHE II score, a revised and simplified version of the original prototype, uses a point score based on initial values of 12 routine physiologic measures, age, and previous health status to provide a general measure of severity of disease. The values recorded are the worst values taken during the patient's first 24 hours in the ICU. The score is applied to one of 34 admission diagnoses to estimate a disease-specific probability of mortality (APACHE II predicted risk of death). The maximum possible APACHE II score is 71, and high scores have been well correlated with mortality. The APACHE II score has been widely used to stratify and compare various groups of critically ill patients, including patients with sepsis, by severity of illness on entry into clinical trials."

A "Brussels score" score is a method for evaluating organ dysfunction as compared to a baseline. If the Brussels score is 2 or greater (ie. moderate, severe, or extreme), then organ failure was recorded as present on that particular day (see TABLE 1C below). In the following description, to correct for deaths during the observation period, days alive and free of organ failure (DAF) were calculated as previously described.

acute lung injury over a defined observation period (28 days). Thus, a lower score for days alive and free of acute lung injury indicates more severe acute lung injury. The reason that days alive and free of acute lung injury is preferable to simply presence or absence of acute lung injury, is that acute lung injury has a high acute mortality and early death (within 28 days) precludes calculation of the presence or absence of acute lung injury in dead patients. The cardiovascular, renal, neurologic, hepatic and coagulation dysfinction were similarly defined as present on each day that the person had moderate, severe or extreme dysfunction as defined by the Brussels score. Days alive and free of steroids are days that a person is alive and is not being treated with exogenous corticosteroids (e.g. hydrocortisone, prednisone, methylprednisolone). Days alive and free of pressors are days that a person is alive and not being treated with intravenous vasopressors (e.g. dopamine, norepinephrine, epinephrine, phenylephrine). Days alive and free of an International Normalized Ratio (INR)>1.5 are days that a person is alive and does not have an INR>1.5.

TABLE 1C

Brussels multiple organ dysfunction (MOD) score

| | | ABNORMAL CLINICALLY SIGNIFICANT ORGAN DYSFUNCTION | | | |
|---|---|---|---|---|---|
| | | Organ Failure Score | | | |
| ORGANS | Normal 0 | Mild 1 | Moderate 2 | Severe 3 | Extreme 4 |
| Cardiovascular Systolic BP (mmHg) | >90 | =90 Responsive to fluid | =90 Unresponsive to fluid | =90 plus pH = 7.3 | =90 plus pH = 7.2 |
| Pulmonary $P_aO_2/F_IO_2$ (mmHg) | >400 | 400-301 | 300-201 Acute lung injury | 200-101 ARDS | =100 Severe ARDS |
| CNS (Glascow Score) | 15 | 14-13 | 12-10 | 9-6 | =5 |
| Coagulation Platelets ($\times 10^5/mm^3$) | >120 | 120-81 | 80-51 | 50-21 | =20 |
| Renal Creatinine (mg/d) | <1.5 | 1.5-1.9 | 2.0-3.4 | 3.5-4.9 | =5.0 |
| Hepatic Bilirubin (mg/d) | <1.2 | 1.2-1.9 | 2.0-5.9 | 6.0-11.9 | =12 |

Round Table Conference on Clinical Trials for the Treatment of Sepsis Brussels, Mar. 12-14, 1994 and Russell J A, Singer J, Bernard G R, Drummond A J, Walley K R, and The Ibuprofen in Sepsis Study Group. Changing pattern of organ dysfunction in early human sepsis is related to mortality. Critical Care Medicine 2000; 28: 3405-3411.

For example, acute lung injury was calculated as follows. Acute lung injury is defined as present when a patient meets all of these four criteria. 1) Need for mechanical ventilation, 2) Bilateral pulmonary infiltrates on chest X-ray consistent with acute lung injury, 3) $PaO_2/FiO_2$ ratio is less than 300, 4) No clinical evidence of congestive heart failure or if a pulmonary artery catheter is in place for clinical purposes, a pulmonary capillary wedge pressure less than 18 mm Hg (1). The severity of acute lung injury is assessed by measuring days alive and free of acute lung injury over a 28 day observation period. Acute lung injury is recorded as present on each day that the person has moderate, severe or extreme dysfunction as defined in the Brussels score. Days alive and free of acute lung injury is calculated as the number of days after onset of acute lung injury that a patient is alive and free of Analysis of variance (ANOVA) is a standard statistical approach to test for statistically significant differences between sets of measurements.

The Fisher exact test is a standard statistical approach to test for statistically significant differences between rates and proportions of characteristics measured in different groups.

2. General Methods

One aspect of the invention may involve the identification of patients or the selection of patients that are either at risk of developing and inflammatory condition or the identification of patients who already have an inflammatory condition. For example, patients who have undergone major surgery or scheduled for or contemplating major surgery may be considered as being at risk of developing an inflammatory condition. Furthermore, patients may be determined as having an inflammatory condition using diagnostic methods and clinical evaluations known in the medical arts. An inflammatory condition, may be selected from the group consisting of: sepsis, septicemia, pneumonia, septic shock, systemic inflammatory response syndrome (SIRS), Acute Respiratory Distress Syndrome (ARDS), acute lung injury, infection, pancreatitis, bacteremia, peritonitis, abdominal abscess, inflammation due to trauma, inflammation due to surgery, chronic inflammatory disease, ischemia, ischemia-reperfusion injury of an organ or tissue, tissue damage due to disease, tissue damage due to chemotherapy or radiotherapy, and reactions to ingested, inhaled, infused, injected, or delivered substances.

Once a patient is identified as being at risk for developing or having an inflammatory condition, then genetic sequence information may be obtained from the patient. Or alternatively genetic sequence information may already have been obtained from the patient. For example, a patient may have already provided a biological sample for other purposes or may have even had their genetic sequence determined in whole or in part and stored for future use. Genetic sequence information may be obtained in numerous different ways and may involve the collection of a biological sample that contains genetic material. Particularly, genetic material, containing the sequence or sequences of interest.

Many methods are known in the art for collecting bodily samples and extracting genetic material from those samples. Genetic material can be extracted from blood, tissue and hair and other samples. There are many known methods for the separate isolation of DNA and RNA from biological material. Typically, DNA may be isolated from a biological sample when first the sample is lysed and then the DNA is isolated from the lysate according to any one of a variety of multi-step protocols, which can take varying lengths of time. DNA isolation methods may involve the use of phenol (Sambrook, J. et al., "Molecular Cloning", Vol. 2, pp. 9.14-9.23, Cold Spring Harbor Laboratory Press (1989) and Ausubel, Frederick M. et al., "Current Protocols in Molecular Biology", Vol. 1, pp. 2.2.1-2.4.5, John Wiley & Sons, Inc. (1994)). Typically, a biological sample is lysed in a detergent solution and the protein component of the lysate is digested with proteinase for 12-18 hours. Next, the lysate is extracted with phenol to remove most of the cellular components, and the remaining aqueous phase is processed further to isolate DNA. In another method, described in Van Ness et al. (U.S. Pat. No. 5,130,423), non-corrosive phenol derivatives are used for the isolation of nucleic acids. The resulting preparation is a mix of RNA and DNA.

Other methods for DNA isolation utilize non-corrosive chaotropic agents. These methods, which are based on the use of guanidine salts, urea and sodium iodide, involve lysis of a biological sample in a chaotropic aqueous solution and subsequent precipitation of the crude DNA fraction with a lower alcohol. The final purification of the precipitated, crude DNA fraction can be achieved by any one of several methods, including column chromatography (Analects, (1994) Vol 22, No. 4, Pharmacia Biotech), or exposure of the crude DNA to a polyanion-containing protein as described in Koller. (U.S. Pat. No. 5,128,247).

Yet another method of DNA isolation, which is described by Botwell, D. D. L. (Anal. Biochem. (1987) 162:463-465) involves lysing cells in 6M guanidine hydrochloride, precipitating DNA from the lysate at acid pH by adding 2.5 volumes of ethanol, and washing the DNA with ethanol.

Numerous other methods are known in the art to isolate both RNA and DNA, such as the one described by Chomczynski (U.S. Pat. No. 5,945,515), whereby genetic material can be extracted efficiently in as little as twenty minutes. Evans and Hugh (U.S. Pat. No. 5,989,431) describe methods for isolating DNA using a hollow membrane filter.

Once a patient's genetic sequence information has been obtained from the patient it may then be further analyzed to detect or determine the identity or genotype of one or more polymorphisms in the protein C gene. Provided that the genetic material obtained, contains the sequence of interest. Particularly, a person may be interested in determining the protein C promoter genotype of a patient of interest, where the genotype includes a nucleotide corresponding to position 2418 or SEQ ID NO.: 1 or position 8 of SEQ ID NO.: 2. The sequence of interest may also include other protein C gene polymorphisms or may also contain some of the sequence surrounding the polymorphism of interest. Detection or determination of a nucleotide identity or the genotype of the single nucleotide polymorphism(s) or other polymorphism, may be accomplished by any one of a number methods or assays known in the art, including but not limited to the following:

Restriction Fragment Length Polymorphism (RFLP) strategy—An RFLP gel-based analysis can be used to distinguish between alleles at polymorphic sites within a gene. Briefly, a short segment of DNA (typically several hundred base pairs) is amplified by PCR. Where possible, a specific restriction endonuclease is chosen that cuts the short DNA segment when one variant allele is present but does not cut the short DNA segment when the other allele variant is present. After incubation of the PCR amplified DNA with this restriction endonuclease, the reaction products are then separated using gel electrophoresis. Thus, when the gel is examined the appearance of two lower molecular weight bands (lower molecular weight molecules travel farther down the gel during electrophoresis) indicates that the initial DNA sample had the allele which could be cut by the chosen restriction endonuclease. In contrast, if only one higher molecular weight band is observed (at the molecular weight of the PCR product) then the initial DNA sample had the allele variant that could not be cut by the chosen restriction endonuclease. Finally, if both the higher molecular weight band and the two lower molecular weight bands are visible then the initial DNA sample contained both alleles, and therefore the patient was heterozygous for this single nucleotide polymorphism;

Sequencing—For example the Maxam-Gilbert technique for sequencing (Maxam A M. and Gilbert W. Proc. Natl. Acad. Sci. USA (1977) 74(4):560-564) involves the specific chemical cleavage of terminally labelled DNA. In this technique four samples of the same labeled DNA are each subjected to a different chemical reaction to effect preferential cleavage of the DNA molecule at one or two nucleotides of a specific base identity. The conditions are adjusted to obtain only partial cleavage, DNA fragments are thus generated in each sample whose lengths are dependent upon the position within the DNA base sequence of the nucleotide(s) which are subject to such cleavage. After partial cleavage is performed, each sample contains DNA fragments of different lengths, each of which ends with the same one or two of the four nucleotides. In particular, in one sample each fragment ends with a C, in another sample each fragment ends with a C or a T, in a third sample each ends with a G, and in a fourth sample each ends with an A or a G. When the products of these four reactions are resolved by size, by electrophoresis on a polyacrylamide gel, the DNA sequence can be read from the pattern of radioactive bands. This technique permits the sequencing of at least 100 bases from the point of labeling. Another method is the dideoxy method of sequencing was published by Sanger et al. (Sanger et al. Proc. Natl. Acad. Sci. USA (1977) 74(12):5463-5467). The Sangermethodrelies on enzymatic activity of a DNA polymerase to synthesize sequence-dependent fragments of various lengths. The lengths of the fragments are determined by the random incorporation of dideoxynucleotide base-specific terminators. These fragments can then be separated in a gel as in the Maxam-Gilbert procedure, visualized, and the sequence determined. Numerous improvements have been made to refine the above methods and to automate the sequencing procedures. Similary, RNA sequencing methods are also known. For example, reverse transcriptase with dideoxy-nucleotides have been used to sequence encephalomyocarditis virus RNA (Zimmern D. and Kaesberg P. Proc. Natl. Acad. Sci. USA (1978) 75(9):4257-4261). Mills D R. and Kramer F R. (Proc. Natl. Acad. Sci. USA (1979) 76(5):2232-2235) describe the use of Q.beta. replicase and the nucleotide analog inosine for sequencing RNA in a chain-termination mechanism. Direct chemical methods for sequencing RNA are also known (Peattie D A. Proc. Nati. Acad. Sci. USA (1979) 76(4):1760-1764). Other methods include those of Donis-Keller et al. (1977, Nucl. Acids Res. 4:2527-2538), Simoncsits A. et al. (Nature (1977) 269 (5631):833-836), Axelrod V D. et al. (Nucl. Acids Res. (1978) 5(10):3549-3563), and Kramer F R. and Mills D R. (Proc. Natl. Acad. Sci. USA (1978) 75(11):5334-5338, which are incorporated herein by reference). Nucleic acid sequences can also be read by stimulating the natural fluoresce of a cleaved nucleotide with a laser while the single nucleotide is contained in a fluorescence enhancing matrix (U.S. Pat. No. 5,674,743);

Hybridization methods for the identification of SNPs using hydridization techniques are described in the U.S. Pat. Nos. 6,270,961 & 6,025,136;

Oligonucleotide ligation assay (OLA)—is based on ligation of probe and detector oligonucleotides annealed to a polymerase chain reaction amplicon strand with detection by an enzyme immunoassay (Villahermosa M L. J Hum Virol (2001) 4(5):238-48; Romppanen E L. Scand J Clin Lab Invest (2001) 61(2):123-9; Iannone M A. et al. Cytometry (2000) 39(2):131-40);

Ligation-Rolling Circle Amplification (L-RCA) has also been successfully used for genotyping single nucleotide polymorphisms as described in Qi X. et al. Nucleic Acids Res (2001) 29(22):E116;

5' nuclease assay has also been successfully used for genotyping single nucleotide polymorphisms (Aydin A. et al. Biotechniques (2001) (4):920-2, 924, 926-8.);

Polymerase proofreading methods are used to determine SNPs identities, as described in WO 0181631; or Allele specific PCR methods have also been successfully used for genotyping single nucleotide polymorphisms (Hawkins J R. et al. Hum Mutat (2002) 19(5):543-553).

Alternatively, if a patient's sequence data is already known, then obtaining may involve retrieval of the patients nucleic acid sequence data from a database, followed by determining or detecting the identity of a nucleic acid or genotype at a polymorphism site by reading the patient's nucleic acid sequence at the polymorphic site.

Once the identity of a polymorphism(s) is determined or detected an indication may be obtained as to patient outcome or prognosis based on the genotype (the nucleotide at the position) of the polymorphism of interest. In the present invention, polymorphisms in the protein C promoter region or other protein C gene polymorphisms, are used to obtain a prognosis or to determine patient outcome. Methods for obtaining patient outcome or prognosis or for patient screening may be useful to determine the ability of a patient to recover from an inflammatory condition. Alternatively, single polymorphism sites or combined polymorphism sites may be used as an indication of a patient's ability to recover from an inflammatory condition, if they are linked to a polymorphism determined to be indicative of a patient's ability to recover from an inflammatory condition.

Once patient outcome or a prognosis is determined, such information may be of interest to physicians and surgeons to assist in deciding between potential treatment options, to help determine the degree to which patients are monitored and the frequency with which such monitoring occurs. Ultimately, treatment decisions may be made in response to factors, both specific to the patient and based on the experience of the physician or surgeon responsible for a patient's care. Treatment options that a physician or surgeon may consider in treating a patient with an inflammatory condition may include, but are not limited to the following:

(a) use of anti-inflammatory therapy;

(b) use of steroids;

(c) use of antibodies to tumor necrosis factor (TNF) or even antibody to endotoxin;

(d) use of tumor necrosis factor receptor (TNF);

(e) use of activated Protein C (Xigris from Lilly);

(f) use of tissue factor pathway inhibitors (tifacogin alpha from Chiron);

(g) use of platelet activating factor hydrolase (PAFase from ICOS); and (h) use of modulators of the coagulation cascade (such as various versions of heparin).

Alternatively, similar methods may be employed to identify new polymorphisms in protein C sequence that correlate with patient outcome or prognosis.

As described above genetic sequence information or genotype information may be obtained from a patient wherein the sequence information contains one or more single nucleotide polymorphism sites in the protein C gene. Also, as previously described the sequence identity of one or more single nucleotide polymorphisms in the protein C gene of one or more patients may then be detected or determined. Furthermore, patient outcome or prognosis may be assessed as described above, for example the APACHE II scoring system or the Brussels score may be used to assess patient outcome or prognosis by comparing patient scores before and after treatment. Once patient outcome or prognosis has been assessed, patient outcome or prognosis may be correlated with the sequence identity of a single nucleotide polymorphism(s). The correlation of patient outcome or prognosis may further include statistical analysis of patient outcome scores and polymorphism(s) for a number of patients.

3. EXAMPLE 1

Patient Outcome or Prognosis in Two Populations using the 2418 Polymorphism (a) Population 1 Sepsis SIRS Inclusion Criteria All patients admitted to the Intensive Care Unit (ICU) between November 2000 and May 2001 were eligible for entry into this study. Patients were excluded if blood could not be obtained for genotype analysis.

Data Collection

Data was recorded for 28 days or until hospital discharge. Raw clinical and laboratory variables were recorded using the worst or most abnormal variable for each 24 hour period with the exception of Glasgow Coma Score, where the best possible score for each 24 hour period was recorded. Missing data on the date of admission was assigned a normal value and missing data after the day one was substituted by carrying forward the previous day's value. Demographic and microbiologic data were recorded. When data collection for each patient was complete, all patient identifiers were removed from all records and the patient file was assigned a unique random number that was cross referenced with the blood samples. The completed raw data file was converted to calculated descriptive and severity of illness scores using standard definitions (i.e. APACHE II and Days alive and free of organ dysfunction calculated using the Brussels criteria).

(b) Population 2 Non-Septic SIRS

Inclusion Criteria

Caucasian patients booked for new elective coronary artery bypass grafting requiring cardiopulmonary bypass (CPB) were included. Patients undergoing urgent or emergency CPB surgery were not included because these patients may have already been exhibiting an inflammatory response to other triggers such as shock. We did not include patients undergoing valve surgery or repeat cardiac surgery because these patients have different pre-operative pathophysiology and often have longer total surgical and CPB times.

After induction of anesthesia and placement of systemic and pulmonary artery catheter (these are routinely inserted for clinical purposes at our institution), blood was obtained prior to CPB for genotyping and for baseline TNF-α, IL-6, IL-8, and IL-10 measurements. In addition, hemodynamic measurements including mean arterial pressure, thermodilutation cardiac outcome, and right arterial pressure as well as height and weight were recorded to calculate systemic vascular resistance index. Systemic Vascular Resistance Index (SVRI) was calculated as the difference between mean arterial pressure and right arterial pressure divided by cardiac index. Blood sampling was repeated at 4 (representing peak response) and 24 hours (to determine if the response is sustained) post-operatively. Hemodynamics to calculate SVRI were measured at zero, 4 and 24 hours post-operatively.

Common Methods—Both Populations

Blood Collection and Processing

Discarded whole blood samples from both populations above, stored at 4° C., were collected from the hospital laboratory. The Buffy coat was extracted and the samples were transferred to 1.5 ml cryotubes, barcoded and cross-referenced with the unique patient number and stored at −80° C. DNA was extracted from the Buffy coat using a QIA amp DNA maxi kit™ (QIAGEN). Patients were genotyped at −1654(2405) and at −1641 (2418) using an RFLP strategy as described by Spek et al. (Blood Coagulation and Fibrinolysis, 5:309-311, 1994). The first PCR strategy used here introduces a BstXI restriction enzyme cut site in the PCR product when a T is present at position −1654 (2405) so that the 246 bp PCR product is cut by BstXI into fragments of 205 and 41 bp. The second PCR strategy also introduces a BstXI restriction enzyme cut site in the PCR product when a G is present at position −1641 (2418) so that the 233 bp PCR product is cut by BstXI into fragments of 193 and 40 bp. After incubation of the PCR amplified DNA with BstXI, the reaction products were then separated using gel electrophoresis.

Statistical Analysis

We compared measures of disease severity using dominant and co-dominant models. We tested for differences between genotype groups using ANOVA for continuous data and a Fisher exact test for discrete data.

Population 1 Septic SIRS—Results

Eighty-one consecutive Caucasian patients admitted to our ICU with SIRS were included in this study. 46.9% of patients were AA homozygotes, 38.3% of patients were AG heterozygotes, and 14.8% of patients were GG homozygotes. The frequency of the A allele was 66% and the frequency of the G allele was 34% and these alleles were in Hardy Weinberg equilibrium in our population. Table 2 shows that there were no significant differences in baseline characteristics between AA, AG, and GG groups. Patients were of similar age, similar sex distribution, had similar admitting APACHE II. Approximately 40% of these patients had sepsis on admission and 10% of these patients had septic shock on admission. Eight percent of these patients developed sepsis at some time during their ICU stay and 45% of these patients developed septic shock at some time during their hospital stay.

TABLE 2

Sepsis SIRS patients baseline characteristics
Baseline Characteristics

| Genotype −1641 (2418) | Age | Sex % Male | Apache II | Sepsis on Admission | S Shock Admission | Sepsis Anytime | S Shock Anytime |
|---|---|---|---|---|---|---|---|
| A A | 58 ± 17 | 55% | 19 ± 9 | 45% | 11% | 84% | 46% |
| A G | 56 ± 15 | 62% | 17 ± 7 | 35% | 3% | 81% | 34% |
| G G | 52 ± 16 | 67% | 20 ± 11 | 42% | 17% | 75% | 50% |
| p (AA vs AG + GG) | 0.34 | 0.75 | 0.47 | 0.49 | 0.58 | 0.98 | 0.64 |

Measurements of days alive and free of SIRS and organ failure suggested a co-dominant effect of allele A. Patients with the A allele demonstrated fewer days alive and free of SIRS (Table 3), DAF acute lung injury and DAF cardiovascular failure (Table 3). Interestingly there was also a significant difference in DAF of the use of steroids. The use of steroids is made on a case by case basis by physicians in our intensive care unit in general and are employed more frequently in patients deemed to have severe sepsis and septic shock. In addition we also noted that the A allele was associated with significantly fewer DAF vasopressors. In addition trends towards adverse outcome or prognosis associated with the A allele were noticed in DAF hepatic failure, DAF renal failure, DAF CNS failure, and DAF International Normalized Ratio (INR)>1.5 (Table 4).

TABLE 3

Sepsis SIRS population: DAF SIRS and Key Organ Failure Key Differences

| Genotype −1641 (2418) | DAF SIRS 4/4 | DAF SIRS 3/4 | DAF Steroids | DAF ALI | DAF CVS | DAF Pressors |
|---|---|---|---|---|---|---|
| A A | 17.6 ± 10.8 | 13.6 ± 11.3 | 12.1 ± 11.9 | 16.8 ± 12.5 | 17.9 ± 11.8 | 16.5 ± 11.5 |
| A G | 22.0 ± 9.8 | 17.6 ± 10.5 | 19.0 ± 11.5 | 20.4 ± 10.6 | 21.8 ± 9.8 | 21.1 ± 10.2 |
| G G | 26.1 ± 3.0 | 22.1 ± 7.4 | 23.8 ± 9.8 | 25.5 ± 4.3 | 26.8 ± 1.4 | 25.2 ± 2.7 |
| p (AA vs AG + GG) | 0.013 | 0.027 | 0.002 | 0.044 | 0.022 | 0.014 |

TABLE 4

Sepsis SIRS Population: DAF Other Organ Failures Other Results

| Genotype −1641 (2418) | DAF Hepatic | DAF Renal | DAF CNS | DAF INR > 1.5 |
|---|---|---|---|---|
| A A | 17.3 ± 12.0 | 17.1 ± 11.9 | 18.5 ± 11.6 | 18.7 ± 11.5 |
| A G | 20.9 ± 9.6 | 19.3 ± 11.6 | 21.3 ± 11.2 | 19.8 ± 10.7 |
| G G | 24.3 ± 7.8 | 20.3 ± 10.0 | 25.6 ± 5.7 | 22.8 ± 9.4 |
| p (AA vs AG + GG | 0.056 | 0.337 | 0.102 | 0.424 |

Most significantly, the A allele was associated with decreased survival (FIG. 1). Patients with the AA genotype had a survival of 58%, those with the AG genotype had a 74% survival, and those with a GG genotype had a 100% survival rate (P<0.017). Thus the protein C −1641 (2418) A allele was associated with decreased survival, more SIRS, worse cardiovascular and respiratory failure and trends to worse failure in other organ systems.

Population 2 Non-Septic SIRS—Results

To confirm these observations and to test for evidence of biological plausibility of the hypothesis that protein C −1641 (2418) A allele is associated with worse SIRS we turned to an independent population. We chose to study 61 Caucasian patients following cardiopulmonary bypass (CPB) surgery. CPB is associated with an inflammatory response that fulfills the definition of SIRS and is correlated with increased inflammatory cytokine expression post-CPB. In this population of 61 Caucasians we found 24 patients of AA genotype, 28 patients of a GG genotype, and 9 patients with GG genotype resulting in an A allele frequency of 62% and G allele frequency of 38%. This population was also in Hardy Weinberg equilibrium. At the preoperative baseline there were no significant differences in age, sex distribution, smokers, diabetes, presence of hypertension, preoperative ejection fraction, bypass time, cross-clamp time, and Aprotinin use (Table 5).

TABLE 5

CPB SIRS: Baseline Characteristics Baseline Characteristics

|  | AA | AG and GG | p |
|---|---|---|---|
| Age | 66.9 ± 12.1 | 65.5 ± 8.6 | 0.60 |
| Sex (% Male) | 79% | 70% | 0.45 |
| Smokers | 17% | 22% | 0.38 |
| Diabetes | 21% | 22% | 0.94 |
| Hypertension | 50% | 57% | 0.61 |
| Pre-op EF | 56 ± 13% | 53 ± 15% | 0.44 |
| Bypass time | 109 ± 43 | 106 ± 39 | 0.81 |
| X clamp time | 82 ± 36 | 79 ± 38 | 0.76 |
| Aprotinin use | 13% | 11% | 0.84 |

Figure 2:
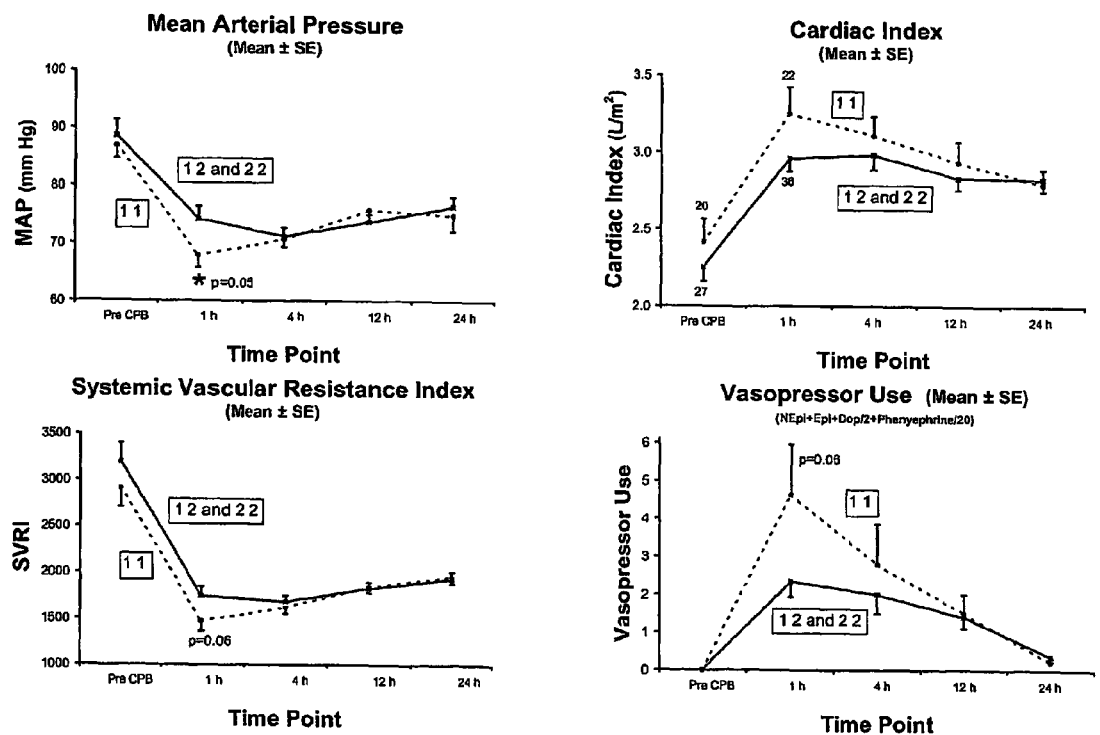
FIG. 2 shows a series of graphs plotting Mean Arterial Pressure (mm Hg) over time before and after cardiopulmonary bypass; Cardiac Index (L/m$^2$) over time before and after cardiopulmonary bypass; Systemic Vascular Resistance Index over time before and after cardiopulmonary bypass; and Vasopressor Use over time before and after cardiopulmonary bypass, with each graph comparing AA homozygotes with AG heterozygotes and GG homozygotes of protein C 2418.
Figure 3:
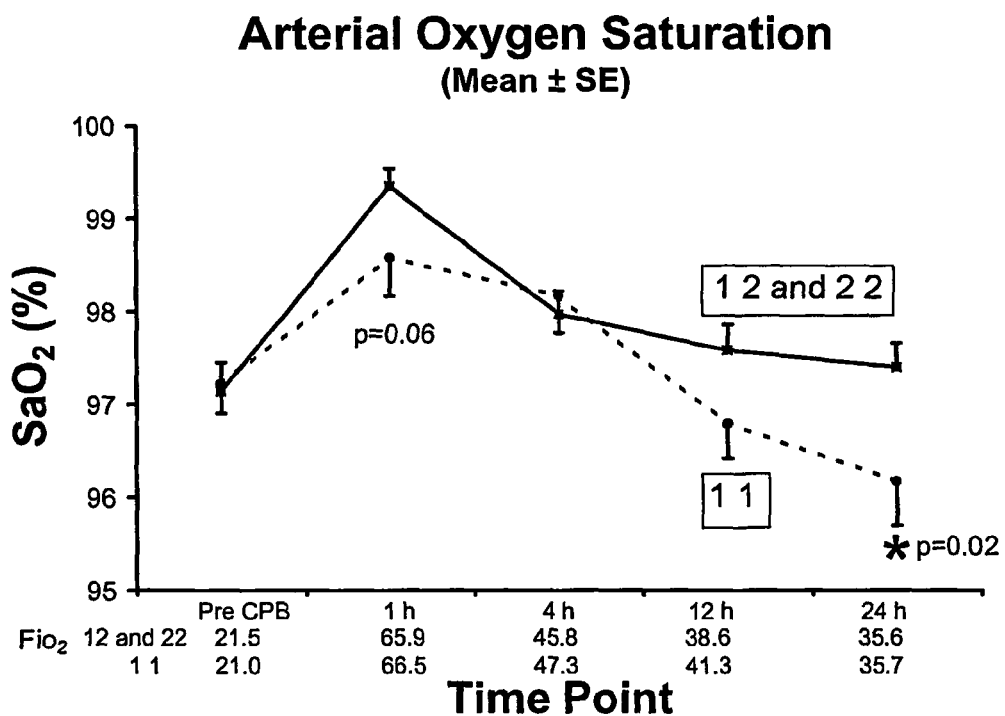
FIG. 3 shows a graph plotting percent Arterial Oxygen Saturation over time before and after cardiopulmonary bypass, comparing AA homozygotes with AG heterozygotes and GG homozygotes of protein C 2418.

Post-operatively 64% of patients with the AA genotype developed an SVRI less than 1500 at least once during first 24 hours while only 50% of other patients developed an SVRI less than 1500. The presence of two consecutive SVRI measurements less than 1500 within the first 24 hours occurred in 32% of patients with the AA genotype and only 19% of other patients (p<0.03). SVRI at 1 hour post CVB was reduced in patients with the AA genotype due to a greater reduction in mean arterial pressure (p<0.05) and greater increase in cardiac index at 1 hour post CPB (FIG. 2). The additional observation of a significantly greater use of vasopressors in patients with the AA genotype at one hour post CPB further amplifies the clinical significance of the excessive vasodilation in patients with the AA genotype post CPB. In addition, arterial oxygen saturation was significantly reduced in patients with the AA genotype over the first 24 hours post CPB (FIG. 3).

Patients with the AA genotype had significantly greater serum IL-6 concentrations at 4 and 24 hours post CPB (Table 6). This was associated with trends towards greater increases in TNF-α, IL-8 and especially IL-10 at 4 and 24 hours post CPB. Thus, the protein C −1641 (2418) A allele was associated with more SIRS as indicated by a lower SVRI, increased pro-inflammatory cytokine response, and worse cardiovascular and respiratory failure post CPB, analogous to those findings in the critically ill SIRS patients.

TABLE 6

CPB SIRS: Post CPB Cytokine Expression Cytokines (pg/mL, Mean ± SE)

|  |  | AA | AG and GG | p |
|---|---|---|---|---|
| TNFα | 4 h | 118 ± 45 | 78 ± 26 | 0.41 |
| TNFα | 24 h | 118 ± 45 | 79 ± 24 | 0.43 |
| IL-6 | 4 h | 1901 ± 795 | 713 ± 148 | 0.08 |
| IL-6 | 24 h | 675 ± 154 | 360 ± 58 | 0.04 |
| IL-8 | 4 h | 133 ± 47 | 121 ± 35 | 0.84 |
| IL-8 | 24 h | 119 ± 52 | 87 ± 29 | 0.57 |

TABLE 6-continued

CPB SIRS: Post CPB Cytokine Expression
Cytokines (pg/mL, Mean ± SE)

|  |  | AA | AG and GG | p |
|---|---|---|---|---|
| IL-10 | 4 h | 119 ± 53 | 42 ± 15 | 0.10 |
| IL-10 | 24 h | 108 ± 54 | 19 ± 7 | 0.06 |

Example Summary

Protein C −1641 (2418) A allele is associated with greater evidence of SIRS and severe cardiovascular and respiratory dysfunction in a critically ill SIRS population and in a post CPB SIRS population. The critically ill SIRS population demonstrates that severe SIRS in the patients with the AA genotype was associated with more severe SIRS and more cardiovascular and respiratory failure (including more acute lung injury, more use of vasopressors, more use of steroids), but also in trends to additional organ system dysfunction and importantly, to decreased survival. These observations were confirmed in an analogous but completely independent SIRS population of critically ill patients. In the CPB population SIRS was induced by cardiac surgery and the cardiopulmonary bypass procedure itself without evidence of infection. Evidence for increased SIRS in those patients having the AA genotype in this population is provided by the observation of greater reduction in SVRI and mean arterial pressure (MAP) and greater vasopressor use at 1 hour post CPB as well as increased inflammatory cytokine expression. The increased inflammatory cytokine expression also provides evidence of biological plausibility in that these cytokines were chosen to be representative of an acute inflammatory response, TNF-α, and integrated inflammatory response (IL-6), chemokine expression associated with lung injury (IL-8), and the counter regulatory anti-inflammatory response (IL-10).

Critically ill patients with the −1641 (2418) A allele had significantly worse outcomes as indicated by lower survival, more SIRS, more severe cardiovascular and respiratory failure, and trends to more severe hepatic renal (p=0.056), neurologic, and coagulation dysfunction. The poor clinical phenotype of the patients who had the −1641 (2418) A allele was also associated with greater use of corticosteroids. It is suspected that the reason for increased use of corticosteroids, is that the clinicians judged that there was a greater need for steroid treatment for severe shock and possibly prolonged respiratory failure. The markedly decreased survival in patients who had the −1641 (2418) A allele is more pronounced than the associated survival associations of most other polymorphisms studied to date in the critically ill.

In summary, the −1641 (2418) A allele is associated with more severe outcomes in the critically ill for both population 1-Septic SIRS and population 2—Non-Septic SIRS, as compared to the −1641 (2418) G allele. Patients with the −1641 (2418) A allele generally showed lower survival, more severe SIRS, and more severe cardiovascular and respiratory failure, more severe organ dysfunction, as compared to the −1641 (2418) G allele patients. Therefore, the −1641 (2418) protein C promoter polymorphism has diagnostic and prognostic use in the critically ill and in patients who are selected for elective CPB and other major surgeries.

4. EXAMPLE 2

Patient Outcome or Prognosis in Two Populations Using the 2405 Polymorphism

Similarly, patients in the above populations were also genotyped at position−1654 (2405) using the RFLP strategy described above. The −1654 (2405) C and T alleles were found not to be associated with patient prognosis or outcome in either the critically ill patients in population 1-Septic SIRS or in population 2-Non-Septic SIRS, as compared to the −1641 (2418) alleles. CC genotype had a survival of 63%, those with the CT genotype had a 71% survival, and those with a TT genotype had a 61% survival rate (P<NS). Therefore, the −1654 (2405) protein C promoter polymorphism does not appear to have diagnostic and prognostic use in the critically ill and in patients who are selected for elective CPB and other major surgeries.

5. EXAMPLE 3

2583 and 2322 Polymorphisms

Similarly the 2322 polymorphism was tested and was found to have no association of genotype with survival; genotype AA had 64% 28 day survival, AG had 72% 28 day survival, and GG had 63% 28 day survival (p NS). In addition, although the 2583 polymorphism was not tested as above, this polymorphism is in total linkage disequilibrium with 2418 as well as with polymorphisms at 1386, 3920, and other combinations of SNPs. For example, the combinations of polymorphisms at 5867+2405 and polymorphisms at 5867+4956 are also linked to 2418. Because these polymorphisms are in linkage disequilibrium with 2418, they show association of genotype with survival, organ dysfinction and a patients ability to respond to subsequent treatment, for example with steroids or vasopressors.

Although the foregoing invention has been described in some detail by way of illustration and example for purposes of clarity of understanding, it will be readily apparent to those of skill in the art in light of the teachings of this invention that changes and modification may be made thereto without departing from the spirit or scope of the appended claims. All patents, patent applications and publications referred to herein are hereby incorporated by reference.

What is claimed is:

1. A method for determining a prognosis for a human subject having, or at risk of developing, an inflammatory condition, the method comprising determining a genotype of said human subject at a polymorphic site in the subject's protein C gene at position 2418 of SEQ ID NO:1, wherein said genotype is indicative of the subject's ability to recover from the inflammatory condition which is SIRS, sepsis or septic shock, wherein the relationship between the nucleotide at said position 2418, the inflammatory condition and the prognosis is as follows:
   (a) for SIRS, sepsis or septic shock:
      (i) sense strand 2418AA homozygosity, or antisense strand 2418TT homozygosity, is prognostic of a decreased ability to recover; and
      (ii) sense strand 2418GG homozygosity, or antisense strand 2418CC homozygosity, is prognostic of an increased ability to recover; and
   (b) for septic SIRS:
      sense strand 2418AG heterozygosity or antisense strand 2418TC heterozygosity is prognostic of an increased ability to recover compared to that of 2418AA homozygosity and a decreased ability to recover compared to that of 2418GG homozygosity.

2. The method of claim 1, further comprising determining the sequence of protein C of the subject.

3. The method of claim 1, wherein the genotype is determined using a nucleic acid sample from the subject.

4. The method of claim 3, which further comprises obtaining the nucleic acid sample from the subject.

5. The method of claim 1, wherein said genotype is determined using one or more of the following techniques:
   (a) restriction fragment length analysis;
   (b) sequencing;
   (c) hybridization;
   (d) oligonucleotide ligation assay;
   (e) ligation rolling circle amplification;
   (f) 5' nuclease assay;
   (g) polymerase proofreading;
   (h) allele specific PCR; and
   (i) reading sequence data.

6. The method of claim 1, wherein the subject is critically ill, and has a genotype prognostic of decreased ability to recover from the inflammatory condition and from severe cardiovascular or respiratory dysfunction present in said inflammatory condition.

7. The method of claim 1, wherein the subject is critically ill, and has a genotype prognostic of increased ability to recover from the inflammatory condition and from mild cardiovascular or respiratory dysfunction present in said inflammatory condition.

8. The method of claim 1, wherein the inflammatory condition is SIRS.

* * * * *

SEQUENCE LISTING

```
<160> NUMBER OF SEQ ID NOS: 11

<210> SEQ ID NO 1
<211> LENGTH: 13870
<212> TYPE: DNA
<213> ORGANISM: Homo sapiens
<220> FEATURE:
```

<221> NAME/KEY: misc_feature
<222> LOCATION: (1386)..(1386)
<223> OTHER INFORMATION: n is a, c, g, or t
<220> FEATURE:
<221> NAME/KEY: misc_feature
<222> LOCATION: (2405)..(2405)
<223> OTHER INFORMATION: n is a, c, g, or t
<220> FEATURE:
<221> NAME/KEY: misc_feature
<222> LOCATION: (2418)..(2418)
<223> OTHER INFORMATION: n is a, c, g, or t
<220> FEATURE:
<221> NAME/KEY: misc_feature
<222> LOCATION: (2583)..(2583)
<223> OTHER INFORMATION: n is a, c, g, or t
<220> FEATURE:
<221> NAME/KEY: misc_feature
<222> LOCATION: (3920)..(3920)
<223> OTHER INFORMATION: n is a, c, g, or t
<220> FEATURE:
<221> NAME/KEY: misc_feature
<222> LOCATION: (4800)..(4800)
<223> OTHER INFORMATION: n is a, c, g, or t
<220> FEATURE:
<221> NAME/KEY: misc_feature
<222> LOCATION: (4919)..(4919)
<223> OTHER INFORMATION: n is a, c, g, or t
<220> FEATURE:
<221> NAME/KEY: misc_feature
<222> LOCATION: (4956)..(4956)
<223> OTHER INFORMATION: n is a, c, g, or t
<220> FEATURE:
<221> NAME/KEY: misc_feature
<222> LOCATION: (5867)..(5867)
<223> OTHER INFORMATION: n is a, c, g, or t
<220> FEATURE:
<221> NAME/KEY: misc_feature
<222> LOCATION: (6187)..(6187)
<223> OTHER INFORMATION: n is a, c, g, or t
<220> FEATURE:
<221> NAME/KEY: misc_feature
<222> LOCATION: (6379)..(6379)
<223> OTHER INFORMATION: n is a, c, g, or t
<220> FEATURE:
<221> NAME/KEY: misc_feature
<222> LOCATION: (9198)..(9198)
<223> OTHER INFORMATION: n is a, c, g, or t
<220> FEATURE:
<221> NAME/KEY: misc_feature
<222> LOCATION: (9534)..(9534)
<223> OTHER INFORMATION: n is a, c, g, or t
<220> FEATURE:
<221> NAME/KEY: misc_feature
<222> LOCATION: (12109)..(12109)
<223> OTHER INFORMATION: n is a, c, g, or t

<400> SEQUENCE: 1

```
gctctctaac tcacagcgag ctcgctgccc aaagtcctgc tccgggggct tcctgggtgg      60
acctgaccgc gttcgggtgc acgtggggcg actcacacct gacaagtaaa gcgggtgagg     120
ccgcgcctgt gaagggcgcc tggctcctcc gcaggacggt gcggcgcggc gccccggct      180 ggaaccaggt gtaactgcag agaccctggg atcgcaggaa cggctggcgg caggactgtc     240
cctacctcga gaaggtgacg gggtttcctg cgctgccagc cgatgaggcg gccgtgacgc     300
agcccgccgt gcagagtccc cgtcggccga caggcgtgca gagctctgca gaggaccctt     360
ccgccctctg ggcagcctgc caagccgtgg caccccaac ccccagcact gggcacttgg      420
gagcattgca gccgccctgg ctcgtaccgg tgccggtgct ttgggcacct gggctggttt     480
ggacatgggt gccccgggca gagtccattt atgcaggtca gaatcagtgt gtggagcctg     540
catagacttg ccctggagcg gctgcctgtg ctggggtggg gaggagtaga gggcgagaag     600
ttggtgggga agggaagcgg cgccaaaaga atacccacaa catcttgcac ctggaaggca     660
```

```
aagcagaggg cagtgatctc tgcagacttg cggggggcgac gcctgaagca aacagggaca    720
tacaagctgg tgccttctgt ggttgtgcat ggggtcttca tgcttcctgt ctgagttccc    780
agaagcttgt ctctgctttt ctaggcagct gccacagcct gtcacaaaca gctcctggtt    840
ctccacttct catagtctcg atttcaaaat ccattgcctc accctccacc tcctctccac    900
ctccacccct cctagcacct cctgactgct tgtgttctgt gtctccccac tgtctcccaa    960
cctggggtgg ggttgggggg gatgtctttc ctcctgtctg ctctttgatg tccagctgaa   1020
gtgtcacctc ctacaggcag cctcccctgg ctatgccagc ttgtactgat tgccctctcc   1080
tctgaattct gtaagcattt cctatgtgta cctgcccctg ggcaaggtgg gcctgacttg   1140
ttagagtgtt agagttttac cctgttcctc taggagggcc tggtaccacc acagcccagc   1200
atggtgtggt gcctcagcag gaggcatctg gttacaatca acacaagctg ttccagccaa   1260
tttaaagaaa cttcaggagg aatagggttt taggagggca tggggaccct cctgcacccg   1320
aagccaggat gtgccaccaa tcataaggag gcaggggcct ccttccgctg ctccctggga   1380
ctctcnaggt gtccgtggcc tcagcccccc tctgcacacc tgcatcttcc ttctcatcag   1440
cttcctctgc tttaagcgta acatggatg cccaggacct ggcctcaatc ttccgagtct   1500
ggtacttatg tgtgactgac agtgtgagac cctactcctc tgatcaatcc cctgggttgg   1560
tgacttccct gtgcaatcaa tggaagccag cgaggcaggg tcacatgccc cgtttagagg   1620
tgcagacttg gagaaggaac gtgggcaagt cttcccagga acaggtaggg cagggaggaa   1680 agggggggcat ctcctggtgca gcccggttcg gagcaggaag acgcttaata aatgctgata   1740
gactgcagga cacaggcaaa ggtgctgagc tggacccttt atttctgccc ttctcccttc   1800
tggcaccccg gccaggaaat tgctgcagcc tttctggaat cccgttcatt tttcttactg   1860
gtccacaaaa ggggccaaat ggaagcagca agacctgagt tcaaattaaa tctgccaact   1920
accagctcag tgaatctggg cgagtaacac aaaacttgag tgtccttacc tgaaaaatag   1980
aggttagagg gatgctatgt gccattgtgt gtgtgtgttg gggtgggga ttggggtga   2040 tttgtgagca attggaggtg agggtggagc ccagtgccca gcacctatgc actgggacc   2100 caaaaaggag catcttctca tgattttatg tatcagaaat tgggatggca tgtcattggg   2160
acagcgtctt ttttcttgta tggtggcaca taaatacatg tgtcttataa ttaatggtat   2220
tttagatttg acgaaatatg aatattacc tgttgtgctg atcttgggca aactataata   2280
tctctgggca aaaatgtccc catctgaaaa acagggacaa cgttcctccc tcagccagcc   2340
actatggggc taaaatgaga ccacatctgt caagggtttt gccctcacct ccctccctgc   2400
tgganggcat ccttggtngg cagaggtggg cttcgggcag aacaagccgt gctgagctag   2460
gaccaggagt gctagtgcca ctgtttgtct atggagaggg aggcctcagt gctgagggcc   2520
aagcaaatat ttgtggttat ggattaactc gaactccagg ctgtcatggc ggcaggacgg   2580
cgnacttgca gtatctccac gacccgcccc tgtgagtccc cctccaggca ggtctatgag   2640
gggtgtggag ggagggctgc ccccgggaga agagagctag gtggtgatga gggctgaatc   2700
ctccagccag ggtgctcaac aagcctgagc ttggggtaaa aggacacaag gccctccaca   2760
ggccaggcct gcagccaca gtctcaggtc cctttgccat cgcctccct ctttccaggc   2820 caagggtccc cagggcccag ggccattcca acagacagtt tggagcccag gaccctccat   2880
tctccccacc ccacttccac ctttgggggt gtcggatttg aacaaatctc agaagcggcc   2940
tcagagggag tcggcaagaa tggagagcag ggtccggtag ggtgtgcaga gggccacgtg   3000
```

```
gcctatccac tggggagggt tccttgatct ctggccacca gggctatctc tgtggccttt   3060
tggagcacct ggtggtttgg ggcagggggtt gaatttccag gcctaaaacc acacaggcct   3120
ggccttgagt cctggctctg cgagtaatgc atggatgtaa acatggagac ccaggacctt   3180
gcctcagtct tccgagtctg gtgcctgcag tgtactgatg gtgtgagacc ctactcctgg   3240
aggatggggg acagaatctg atcgatcccc tgggttggtg acttccctgt gcaatcaacg   3300
gagaccagca agggttggat ttttaataaa ccacttaact cctccgagtc tcagtttccc   3360
cctctatgaa atggggttga cagcattaat aactacctct tgggtggttg tgagccttaa   3420
ctgaagtcat aatatctcat gtttactgag catgagctat gtgcaaagcc tgttttgaga   3480
gctttatgtg gactaactcc tttaattctc acaacaccct ttaaggcaca gatacaccac   3540
gttattccat ccattttaca aatgaggaaa ctgaggcatg gagcagttaa gcatcttgcc   3600
caacattgcc ctccagtaag tgctggagct ggaatttgca ccgtgcagtc tggcttcatg   3660
gcctgccctg tgaatcctgt aaaaattgtt tgaaagacac catgagtgtc caatcaacgt   3720
tagctaatat tctcagccca gtcatcagac cggcagaggc agccacccca ctgtccccag   3780
ggaggacaca aacatcctgg caccctctcc actgcattct ggagctgctt tctaggcagg   3840
cagtgtgagc tcagccccac gtagagcggg cagccgaggc cttctgaggc tatgtctcta   3900
gcgaacaagg accctcaatn ccagcttccg ccctgacggc cagcacacag ggacagccct   3960
ttcattccgc ttccacctgg gggtgcaggc agagcagcag cggggtgtagg cactgcccgg   4020 agctcagaag tcctcctcag acaggtgcca gtgcctccag aatgtggcag ctcacaagcc   4080
tcctgctgtt cgtggccacc tggggaattt ccggcacacc agctcctctt ggtaaggcca   4140
ccccacccct accccgggac ccttgtggcc tctacaaggc ctggtggcat ctgcccaggc   4200
cttcacagct tccaccatct ctctgagccc tgggtgaggt gaggggcaga tgggaatggc   4260
aggaatcaac tgacaagtcc caggtaggcc agctgccaga gtgccacaca ggggctgcca   4320
gggcaggcat gcgtgatggc agggagcccc gcgatgacct cctaaagctc cctcctccac   4380
acggggatgg tcacagagtc ccctgggcct tccctctcca cccactcact ccctcaactg   4440
tgaagacccc aggcccaggc taccgtccac actatccagc acagcctccc ctactcaaat   4500
gcacactggc ctcacggctg ccctgcccca acccctttcc tggtctccac agccaacggg   4560
aggaggccat gattcttggg gaggtccgca ggacacatgg gcccctaaag ccacaccagg   4620
ctgttggttt catttgtgcc tttatagagc tgtttatctg cttgggacct gcacctccac   4680
cctttcccaa ggtgccctca gctcaggcat accctcctct aggatgcctt ttcccccatc   4740
ccttcttgct cacaccccca acttgatctc tccctcctaa ctgtgccctg cacccaagan   4800
agacacttca cagagcccag gagacacctg gggaccttc ctgggtgata ggtctgtcta   4860
tcctccaggt gtccctgccc aaggggagaa gcatgggaa tacttggttg ggggaggana   4920
ggaagactgg ggggatgtgt caagatgggg ctgcangtgg tgtactggca gaagagtgag   4980
aggatttaac ttggcagcct ttacagcagc agccagggct tgagtactta tctctgggcc   5040
agggactgta ttggatgttt tacatgacgg tctcatcccc atgttttttgg atgagtaaat   5100 tgaaccttag aaaggtaaag acactggctc aaggtcacac agagatcggg gtggggttca   5160
cagggaggcc tgtccatctc agagcaaggc ttcgtcctcc aactgccatc tgcttcctgg   5220
ggaggaaaag agcagaggac ccctgcgcca agccatgacc tagaattaga atgagtcttg   5280 aggggggcgga gacaagacct tcccaggctc tcccagctct gcttcctcag acccctcat   5340 ggccccagcc cctcttaggc ccctccacca aggtgagctc cccctcccctc caaaaccaga   5400
```

```
ctcagtgttc tccagcagcg agcgtgccca ccaggtgctg cggatccgca aacgtgccaa    5460
ctccttcctg gaggagctcc gtcacagcag cctggagcgg gagtgcatag aggagatctg    5520
tgacttcgag gaggccaagg aaattttcca aaatgtggat gacacagtaa ggccaccatg    5580
ggtccagagg atgaggctca ggggcgagct ggtaaccagc aggggcctcg aggagcaggt    5640
ggggactcaa tgctgaggcc ctcttaggag ttgtgggggt ggctgagtgg agcgattagg    5700
atgctggccc tatgatgtcg gccaggcaca tgtgactgca agaaacagaa ttcaggaaga    5760
agctccagga aagagtgtgg ggtgaccctg gtggggact cccaccagcc acagtgtagg     5820
tggttcagtc caccctccag ccactgctga gcaccactgc ctccccntcc cacctcacaa    5880
agaggggacc taaagaccac cctgcttcca cccatgcctc tgctgatcag ggtgtgtgtg    5940
tgaccgaaac tcacttctgt ccacataaaa tcgctcactc tgtgcctcac atcaaaggga    6000
gaaaatctga ttgttcaggg ggtcggaaga cagggtctgt gtcctatttg tctaagggtc    6060
agagtccttt ggagccccca gagtcctgtg gacgtggccc taggtagtag ggtgagcttg    6120
gtaacggggc tggcttcctg agacaaggct cagacccgct ctgtccctgg ggatcgcttc    6180
agccacnagg acctgaaaat tgtgcacggc ctgggccccc ttccaaggca tccagggatg    6240 cttttccagtg gaggctttca gggcaggaga ccctctggcc tgcaccctct cttgccctca    6300
gcctccacct ccttgactgg accccatct ggacctccat ccccaccacc tctttcccca     6360
gtggcctccc tggcagacnc cacagtgact ttctgcaggc acatatctga tcacatcaag    6420
tccccaccgt gctcccacct cacccatggt ctctcagccc cagcaggcct tggctggcct    6480
ctctgatgga gcaggcatca ggcacaggcc gtgggtctca acgtgggctg ggtggtcctg    6540
gaccagcagc agccgccgca gcagcaaccc tggtacctgg ttaggaacgc agaccctctg    6600
cccccatcct cccaactctg aaaaacactg gcttaggaa aggcgcgatg ctcaggggtc      6660
ccccaaagcc cgcaggcaga gggagtgatg ggactggaag gaggccgagt gacttggtga    6720
gggattcggg tcccttgcat gccagaggct gctgtgggag cggacagtcg cgagagcagc    6780
actgcagctg catggggaga gggtgttgct ccagggacgt gggatggagg ctgggcgcgg    6840
gcgggtggcg ctggagggcg ggggagggc agggagcacc agctcctagc agccaacgac      6900
catcgggcgt cgatccctgt tgtctggaa gccctcccct cccctgcccg ctcacccgct       6960
gccctgcccc acccgggcgc gccccctccg cacaccggct gcaggagcct gacgctgccc    7020
gctctctccg cagctggcct tctggtccaa gcacgtcggt gagtgcgttc tagatccccg    7080
gctggactac cggcgcccgc gcccctcggg atctctggcc gctgacccc taccccgcct      7140 tgtgtcgcag acggtgacca gtgcttggtc ttgcccttgg agcacccgtg cgccagcctg    7200
tgctgcgggc acggcacgtg catcgacggc atcggcagct tcagctgcga ctgccgcagc    7260
ggctgggagg gccgcttctg ccagcgcggt gaggggagga ggtggatgct ggcgggcggc    7320
ggggcggggc tggggccggg ttggggcgc ggcaccagca ccagctgccc gcgccctccc     7380
ctgcccgcag aggtgagctt cctcaattgc tcgctggaca acggcggctg cacgcattac    7440
tgcctagagg aggtgggctg gcggcgctgt agctgtgcgc ctggctacaa gctggggggac  7500 gacctcctgc agtgtcaccc cgcaggtgag aagcccccaa tacatcgccc aggaatcacg    7560
ctgggtgcgg ggtgggcagg cccctgacgg ggcgcggcgc ggggggctca ggagggtttc    7620
tagggaggga gcgaggaaca gagttgagcc ttggggcagc ggcagacgcg ccccaacacc    7680
ggggccactg ttagcgcaat cagcccggga gctgggcgcg ccctccgctt tccctgcttc    7740
```

```
ctttcttcct ggcgtccccg ccttcctccg ggcgccccct gcgcacctgg ggccacctcc   7800
tggagcgcaa gcccagtggt ggctccgctc cccagtctga gcgtatctgg ggcgaggcgt   7860
gcagcgtcct cctccatgta gcctggctgc gttttctctc tgacgttgtcc ggcgtgcatc   7920 gcatttccct ctttacccccc ttgcttcctt gaggagagaa cagaatcccg attctgcctt   7980
cttctatatt ttccttttta tgcattttaa tcaaatttat atatgtatga aactttaaaa   8040
atcagagttt tacaactctt acatttcagc atgctgttcc ttggcatggg tcctttttc    8100 attcattttc attaaaaggt ggaccctttt aatgtggaaa ttcctatctt ctgcctctag   8160 ggacattat cacttatttc ttctacaatc tcccctttac ttcctctatt ttctctttct   8220
ggacctccca ttattcagac ctctttcctc tagttttatt gtctcttcta tttcccatct   8280
ctttgacttt gtgttttctt tcagggaact ttctttttt tctttttttt tgagatggag    8340
tttcactctt gttgtcccag gctggagtgc aatgacgtga tctcagctca ccacaacctc   8400
cgcctcctgg attcaagcga ttctcctgcc gcagcctccc gagtagctgg gattacaggc   8460
atgcgccacc acgcccagct aattttgtgt ttttagtaga aaggggttt ctccgtgttg    8520 gtcaagctgg tcttgaactc ctgacctcag gtgatccacc tgccttggcc tcctaaagtg   8580
ctgggattac aggcgtgagc caccgcgccc agcctctttc agggaacttt ctacaacttt   8640
ataattcaat tcttctgcag aaaaaaattt tggccaggc tcagtagctc agaccaataa    8700
ttccagcact ttgagaggct gaggtgggag gattgcttga gcttgggagt ttgagactag   8760
cctgggcaac acagtgagac cctgtctcta tttttaaaaa aagtaaaaaa agatctaaaa   8820
atttaacttt ttatttgaa ataattagat atttccagga agctgcaaag aaatgcctgg    8880
tgggcctgtt ggcctgtggg tttcctgcaa ggccgtggga aggccctgtc attggcagaa   8940
ccccagatcg tgagggcttt cctttaggc tgctttctaa gaggactcct ccaagctctt    9000
ggaggatgga agacgctcac ccatggtgtt cggcccctca gagcagggtg gggcagggga   9060
gctggtgcct gtgcaggctg tggacatttg catgactccc tgtggtcagc taagagcacc   9120
actccttcct gaagcggggc ctgaagtccc tagtcagagc ctctggttca ccttctgcag   9180
gcagggagag gggagtcnag tcagtgagga gggctttcgc agtttctctt acaaactctc   9240
aacatgccct cccacctgca ctgccttcct ggaagcccca cagcctccta tggttccgtg   9300
gtccagtcct tcagcttctg ggcgccccca tcacgggctg agatttttgc tttccagtct   9360
gccaagtcag ttactgtgtc catccatctg ctgtcagctt ctggaattgt tgctgttgtg   9420 cccttttccat tcttttgtta tgatgcagct ccctgctga cgacgtccca ttgctctttt   9480
aagtctagat atctggactg ggcattcaag gcccattttg agcagagtcg ggcngacctt   9540
tcagccctca gttctccatg gagtatgcgc tctcttcttg gcaggaggc ctcacaaaca    9600 tgccatgcct attgtaggag ctctccaaga atgctcacct ccttctccct gtaattcctt   9660
tcctctgtga ggagctcagc agcatcccat tatgagacct tactaatccc agggatcacc   9720
cccaacagcc ctggggtaca atgagctttt aagaagttta accacctatg taaggagaca   9780
caggcagtgg gcgatgctgc ctggcctgac tcttgccatt gggtggtact gtttgttgac   9840
tgactgactg actgactgga gggggtttgt aatttgtatc tcagggatta ccccaacag    9900 ccctgggta caatgagcct tcaagaagtt taacaaccta tgtaaggaca cacagccagt    9960
gggtgatgct gcctggtctg actcttgcca ttcagtggca ctgtttgttg actgactgac  10020
tgactgactg gctgactgga gggggttcat agctaatatt aatggagtgg tctaagtatc  10080
attggttcct tgaaccctgc actgtggcaa agtggcccac aggctggagg aggaccaaga  10140
```

```
caggagggca gtctcgggag gagtgcctgg caggcccctc accacctctg cctacctcag    10200
tgaagttccc ttgtgggagg ccctggaagc ggatggagaa gaagcgcagt cacctgaaac    10260
gagacacaga agaccaagaa gaccaagtag atccgcggct cattgatggg aagatgacca    10320
ggcggggaga cagcccctgg caggtgggag gcgaggcagc accggctgct cacgtgctgg    10380
gtccgggatc actgagtcca tcctggcagc tatgctcagg gtgcagaaac cgagagggaa    10440
gcgctgccat tgcgtttggg ggatgatgaa ggtgggggat gcttcaggga agatggacg     10500
caacctgagg ggagaggagc agccaggvtg ggtgagggga ggggcatggg ggcatggagg    10560
ggtctgcagg agggagggtt acagtttcta aaaagagctg gaaagacact gctctgctgg    10620
cgggatttta ggcagaagcc ctgctgatgg gagagggcta ggagggaggg ccgggcctga    10680
gtacccctcc agcctccaca tgggaactga cacttactgg gttcccctct ctgccaggca    10740
tgggggagat aggaaccaac aagtgggagt atttgccctg gggactcaga ctctgcaagg    10800
gtcaggaccc caaagacccg gcagcccagt gggaccacag ccaggacggc ccttcaagat    10860
agggggctgag ggaggcccaa ggggaacatc caggcagcct gggggccaca aagtcttcct    10920
ggaagacaca aggcctggcc aagcctctaa ggatgagagg agctcgctgg gcgatgttgg    10980
gtgtggctga gggtgactga aacagtatga acagtgcagg aacagcatgg gcaaaggcag    11040
gaagacaccc tgggacaggc tgacactgta aaatgggcaa aaatagaaaa cgccagaaag    11100
ggcctaagcc tatgcccata tgaccaggga acccaggaaa gtgcatatga aacccaggtg    11160
ccctggactg gaggctgtca ggaggcagcc ctgtgatgtc atcatcccac cccattccag    11220
gtggtcctgc tggactcaaa gaagaagctg gcctgcgggg cagtgctcat ccacccctcc    11280
tgggtgctga cagcggccca ctgcatggat gagtccaaga agctccttgt caggcttggt    11340
atgggctgga gccaggcaga aggggctgc caggagcctg ggtaggggga ccaggcaggc    11400
tgttcaggtt tggggggaccc cgctccccag gtgcttaagc aagaggcttc ttgagctcca    11460
cagaaggtgt ttggggggaa gaggcctatg tgccccacc ctgcccaccc atgtacaccc    11520
agtattttgc agtagggggt tctctggtgc cctcttcgaa tctgggcaca ggtacctgca    11580
cacacatgtt tgtgaggggc tacacagacc ttcacctctc cactcccact catgaggagc    11640
aggctgtgtg ggcctcagca cccttgggtg cagagaccag caaggcctgg cctcagggct    11700
gtgcctccca cagactgaca gggatggagc tgtacagagg gagccctagc atctgccaaa    11760
gccacaagct gcttccctag caggctgggg gcacctatgc attggcccccg atctatggca    11820
atttctggag ggggggtctg gctcaactct ttatgccaaa aagaaggcaa agcatattga    11880
gaaaggccaa attcacattt cctacagcat aatctatggc cagtgccccc ccgtgggggct    11940
tggcttagaa ttcccaggtg ctcttcccag ggaaccatca gtctggactg agaggaccct    12000
ctctctcagg tgggacccgg ccctgtcctc cctggcagtg ccgtgttctg ggggtcctcc    12060
tctctgggtc tcactgcccc tggggtctct ccagctacct ttgctccang ttcctttgtg    12120
gctctggtct gtgtctgggg tttccagggg tctcggggctt cctgctgcc cattccttct    12180
ctggtctcac ggctccgtga ctcctgaaaa ccaaccagca tcctaccccct ttgggattga    12240
cacctgttgg ccactccttc tggcaggaaa agtcaccgtt gatagggttc cacggcatag    12300
acaggtggct ccgcgccagt gcctgggacg tgtgggtgca cagtctccgg gtgaaccttc    12360
ttcaggccct ctgcccaggc ctgcaggggc acagcagtgg gtgggcctca ggaaagtgcc    12420
actggggaga ggctcccgc agcccactct gactgtgccc tctgccctgc aggagagtat    12480
```

-continued

```
gacctgcggc gctgggagaa gtgggagctg gacctggaca tcaaggaggt cttcgtccac    12540
cccaactaca gcaagagcac caccgacaat gacatcgcac tgctgcacct ggcccagccc    12600
gccaccctct cgcagaccat agtgcccatc tgcctcccgg acagcggcct tgcagagcgc    12660
gagctcaatc aggccggcca ggagaccctc gtgacgggct ggggctacca cagcagccga    12720
gagaaggagg ccaagagaaa ccgcaccttc gtcctcaact tcatcaagat tcccgtggtc    12780
ccgcacaatg agtgcagcga ggtcatgagc aacatggtgt ctgagaacat gctgtgtgcg    12840
ggcatcctcg ggaccggca ggatgcctgc gagggcgaca gtgggggcc catggtcgcc     12900
tccttccacg gcacctggtt cctggtgggc ctggtgagct ggggtgaggg ctgtgggctc    12960
cttcacaact acggcgttta caccaaagtc agccgctacc tcgactggat ccatgggcac    13020
atcagagaca aggaagcccc ccagaagagc tgggcacctt agcgaccctc cctgcagggc    13080
tgggcttttg catggcaatg gatgggacat taaagggaca tgtaacaagc acaccggcct    13140
gctgttctgt ccttccatcc ctcttttggg ctcttctgga gggaagtaac atttactgag    13200
cacctgttgt atgtcacatg ccttatgaat agaatcttaa ctcctagagc aactctgtgg    13260
ggtggggagc agcagatcca agttttgcgg ggtctaaagc tgtgtgtgtt gaggggata    13320
ctctgtttat gaaaaagaat aaaaaacaca accacgaagc cactagagcc ttttccaggg    13380
cttggaag agcctgtgca agccggggat gctgaaggtg aggcttgacc agcttttccag    13440
ctagcccagc tatgaggtag acatgtttag ctcatatcac agaggaggaa actgaggggt    13500
ctgaaaggtt tacatggtgg agccaggatt caaatctagg tctgactcca aaacccaggt    13560
gcttttttct gttctccact gtcctggagg acagctgttt cgacggtgct cagtgtggag    13620
gccactatta gctctgtagg gaagcagcca gagacccaga aagtgttggt tcagcccaga    13680
atgagctcac agtgtcgcgg gggaagctgt ttaagaacaa tgttacacca tcatgaacag    13740
cagtaagaaa gaggctctgg cttaacctgg cctgataggc ctaattgaat gagacagaaa    13800
taagtcaagg atgctctgat ttgaaatcat gaagtacctg atgaaaagaa atggtggtga    13860
gataaagctg                                                          13870
```

<210> SEQ ID NO 2
<211> LENGTH: 20
<212> TYPE: DNA
<213> ORGANISM: Homo sapiens
<220> FEATURE:
<221> NAME/KEY: misc_feature
<222> LOCATION: (8)..(8)
<223> OTHER INFORMATION: n is a, c, g, or t

<400> SEQUENCE: 2
ccttggtngg cagaggtggg                                               20

<210> SEQ ID NO 3
<211> LENGTH: 20
<212> TYPE: DNA
<213> ORGANISM: Homo sapiens
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 3
tgganggcat ccttggtngg                                               20

<210> SEQ ID NO 4
<211> LENGTH: 20
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t

<400> SEQUENCE: 4
nggcagaggt gggcttcggg                                               20

<210> SEQ ID NO 5
<211> LENGTH: 30
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t

<400> SEQUENCE: 5
nggcagaggt gggcttcggg cagaacaagc                                    30

<210> SEQ ID NO 6
<211> LENGTH: 20
<212> TYPE: DNA
<213> ORGANISM: Homo sapiens
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 6
gctgganggc atccttggtn                                               20

<210> SEQ ID NO 7
<211> LENGTH: 30
<212> TYPE: DNA
<213> ORGANISM: Homo sapiens
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t

<400> SEQUENCE: 7
ctccctccct gctgganggc atccttggtn                                    30

<210> SEQ ID NO 8
<211> LENGTH: 40
<212> TYPE: DNA
<213> ORGANISM: Homo sapiens
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t

```
-continued

<400> SEQUENCE: 8
ttgccctcac ctccctccct gctgganggc atccttggtn                    40

<210> SEQ ID NO 9
<211> LENGTH: 90
<212> TYPE: DNA
<213> ORGANISM: Homo sapiens
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t

<400> SEQUENCE: 9
caagggtttt gccctcacct ccctccctgc tgganggcat ccttggtngg cagaggtggg    60
cttcgggcag aacaagccgt gctgagctag                                    90

<210> SEQ ID NO 10
<211> LENGTH: 16
<212> TYPE: DNA
<213> ORGANISM: Homo sapiens
<220> FEATURE:
<221> NAME/KEY: misc_feature
<222> LOCATION: (8)..(8)
<223> OTHER INFORMATION: n is a, c, g, or t

<400> SEQUENCE: 10
ccttggtngg cagagg                                              16

<210> SEQ ID NO 11
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: n is a, c, g, or t

<400> SEQUENCE: 11
cttggtnggc ag                                                  12
```